(12) United States Patent
Chelliserry et al.

(10) Patent No.: US 10,093,989 B2
(45) Date of Patent: Oct. 9, 2018

(54) RED BLOOD CELL LYSIS SOLUTION

(71) Applicant: Gen-Probe Incorporated, San Diego, CA (US)

(72) Inventors: Jijumon Chelliserry, San Diego, CA (US); Kui Gao, San Diego, CA (US); Jeffrey M. Linnen, Poway, CA (US)

(73) Assignee: GEN-PROBE INCORPORATED, San Diego, CA (US)

( * ) Notice: Subject to any disclaimer, the term of this patent is extended or adjusted under 35 U.S.C. 154(b) by 96 days.

(21) Appl. No.: 14/918,131

(22) Filed: Oct. 20, 2015

(65) Prior Publication Data

US 2016/0201144 A1 Jul. 14, 2016

Related U.S. Application Data

(60) Provisional application No. 62/066,244, filed on Oct. 20, 2014.

(51) Int. Cl.
| | |
|---|---|
| C12Q 1/68 | (2018.01) |
| C12Q 1/6893 | (2018.01) |
| C12N 1/06 | (2006.01) |
| G01N 33/48 | (2006.01) |

(52) U.S. Cl.
CPC ............. *C12Q 1/6893* (2013.01); *C12N 1/06* (2013.01); *G01N 33/48* (2013.01); *C12Q 2600/158* (2013.01)

(58) Field of Classification Search
CPC .. C12N 1/06; C12Q 1/6893; C12Q 2600/158; G01N 33/48
USPC ......................................................... 435/6.1
See application file for complete search history.

(56) References Cited

U.S. PATENT DOCUMENTS

| | | | |
|---|---|---|---|
| 4,843,155 A | 6/1989 | Chomczynski | |
| 5,346,994 A | 9/1994 | Chomczynski | |
| 5,945,515 A | 8/1999 | Chomczynski | |
| 5,973,137 A * | 10/1999 | Heath ................ | C12N 15/1003 435/91.3 |
| 6,111,096 A | 8/2000 | Laugharn et al. | |
| 7,601,491 B2 | 10/2009 | Collis et al. | |
| 7,670,768 B1 | 3/2010 | Heath et al. | |
| 2001/0041332 A1 | 11/2001 | Hillebrand et al. | |
| 2002/0068280 A1 | 6/2002 | Fairman | |
| 2004/0142318 A1 | 7/2004 | Wu et al. | |
| 2005/0208501 A1 | 9/2005 | Goldrick | |
| 2006/0063185 A1 * | 3/2006 | Vannier ................. | C07K 16/20 435/6.15 |
| 2007/0281317 A1 | 12/2007 | Becker et al. | |
| 2009/0081678 A1 | 3/2009 | Ryan et al. | |
| 2009/0143572 A1 | 6/2009 | Inomata et al. | |
| 2011/0092687 A1 * | 4/2011 | Bendzko ............ | C12N 15/1003 536/23.1 |
| 2011/0183398 A1 * | 7/2011 | Dasaratha ........ | G01N 33/54333 435/178 |
| 2012/0164644 A1 * | 6/2012 | Neely .................... | G01N 24/08 435/6.11 |
| 2014/0087359 A1 | 3/2014 | Njoroge et al. | |

FOREIGN PATENT DOCUMENTS

| | | | |
|---|---|---|---|
| EP | 87117540.2 A | | 6/1988 |
| JP | 2007132776 A | | 5/2007 |
| WO | WO 02055737 | * | 7/2002 |
| WO | 2012054588 A2 | | 4/2012 |

OTHER PUBLICATIONS

Zheng et al., Clinical Chemistry, 52(7): 1-8, (Year: 2006).*
Chomczynski et al., "Single-Step Method of RNA Isolation by Acid Guanidinium Thiocyanate-Phenol-Chloroform Extraction," Analytical Biochemistry, 1987, 162:156-159, Academic Press, Inc., USA.
Guenther, et al., "Implementation of a proficiency testing for the assessment of the preanalytical phase of blood samples used for RNA based analysis," Clin Chim Acta, 413, 2012, 779-786, Amsterdam, Elsevier.
Roche, "Red Blood Cell Lysis Buffer," Cat. No. 11 814 389 001, "For preferential lysis of red blood cells from human whole blood," Version 08, 2011.
Guenther, et al. "Spidia-RNA: First external quality assessment for the pre-analytical phase of blood samples used for RNA based analyses," Methods 59, 2013, 20-31.
Ovstebo, et al. "Qualification of relative changes in specific mRNAs from frozen whole blood—methodological considerations and clinical implications," Clin Chem Lab Med, 2007, 45:171-176, Berlin ; New York : Walter De Gruyter, c1998.
PCT International Search Report, International Application No. PCT/US2015/056480, dated Jan. 4, 2016.
PCT Written Opinion, International Application No. PCT/US2015/056480, dated Jan. 4, 2016.
UKIPO Search and Examination Report, Application No. GB1518583.8, dated Jul. 22, 2016.
UKPO Combined Search and Examination Report under Sections 17 and 18(3), U.K. Application No. GB1800795.5, dated Feb. 5, 2018.
Teal et al., "A New Real-Time PCR Assay for Improved Detection of the Parasite *Babesia microti*," Journal of Clinical Microbiology, vol. 50, No. 3, 2011.
EPO Extended European Search Report, European Application No. 15851970.2, dated Apr. 23, 2018.

* cited by examiner

*Primary Examiner* — Cynthia B Wilder
(74) *Attorney, Agent, or Firm* — Jeffrey E. Landes; Nicholas V. Sherbina

(57) ABSTRACT

The invention provides a lysis reagent for lysing red blood cells, thereby releasing a target, such as RNA from a parasitic organism, in a form suitable for analysis. The reagent includes at least ammonium chloride and an anionic detergent, and may include an anti-coagulant. The reagent serves to lyse red blood cells, protect the released target from degradation in the lysate, and is compatible with subsequent steps for analysis of the target such as target capture, amplification, detection, or sequencing.

20 Claims, 12 Drawing Sheets
Specification includes a Sequence Listing.

| Lysis buffers | Stabilizing agent TDTMABr/250mM Tartaric Acid | RBC Lysis agent NH4Cl/NaHCO3 | Lysing/Stabilizing Tween-20 | RNase inhibitor Beta-Mercaptoethanol (BME) | Lysing/Stabilizing LLS | pH | TCR Protein | TCR Aptima |
|---|---|---|---|---|---|---|---|---|
| PAXgene lysis soln | x | | | | | 3.8 | PPT | |
| PTM1.0 | x | | | | | 4.0 | PPT | |
| PTM1.1(5% Tween) | x | | x | | | 4.0 | PPT | |
| PTM1.2 (10% Tween) | x | | x | | | 4.0 | PPT | |
| PTM4.0 (Paxgene+BME) | x | | x | x | | 3.8 | PPT | |
| Roche RBC lysis Buffer | | x | | | | 7.5 | | |
| Homebrew RBC Lysis buffer | | x | | | | 7.5 | | |
| PTM2.0 | x | x | x | | | 4.2 | PPT | |
| PTM2.1 | x | x | x | x | | 4.3 | PPT | |
| PTM2.2 | x | x | x | x | | - | PPT | |
| PTM2.3 | | x | | x | | 7.5 | NT | NT |
| PTM2.4 (5% LLS) | | x | | | x | 7.4 | | |
| IC Buffer (10% LLS) | | | | | x | 7.4 | | |
| PTM3.0 (IC8+BME) | | | | x | x | 7.4 | | |
| Saponin | | | | | | 4.5 | | |
| Saponin + 5% Tween | | | x | | | 4.5 | | |

Legend:
- Best condition
- OK condition
- Activity is variable (depends on age of blood)
- No or diminished activity
- PPT — A precipitate
- TDTMAO — tetradecyltrimethylammonium oxalate
- TDTMAB — tetradecyltrimethylammonium bromide
- NT — Not tested

FIG. 3

RED BLOOD CELL LYSIS SOLUTION

BACKGROUND

Although there are commercial assays for detecting RNA in blood, the RNA detected in such assays is usually present in extracellular forms, such as HIV or HCV particles in the blood. Detection of RNA or other target molecules from within red blood cells is more challenging. Reagents used in lysis may interfere with subsequent processing as many non-target molecules released by lysis, particularly nucleases or proteases, may degrade target molecules.

The intrinsic instability of RNA and presence of RNAses in whole blood makes isolation of RNA a difficult task. The use of high purity, intact RNA facilitates sensitive clinical diagnostic assays. Existing approaches typically involve several sequential steps: a step to disrupt the cells, a step to denature the proteins, another step for the stabilization and protection of RNA from RNAses, and then a step for isolation of the RNA Tetradecyltrimethylammonium oxalate (TDTMAO) is commonly used for transport, storage and processing of blood (U.S. Pat. Nos. 6,602,718 and 6,617,170). This quaternary amine is contained, for example, in the PAXgene™ Blood RNA System (BD Biosciences) and works by penetrating the cell and stabilizing intracellular target RNA. The RNA can then be later purified and analyzed from the components of whole blood using standard techniques. Methods for lysing cells and inhibiting RNases using guanidinium salts are also known (Chomczynski et al. (1987) Anal. Biochem. 162, 156-159).

Human Babesiosis is an emerging infectious disease resulting from a tick-borne intraerythrocytic infection of red blood cells. *Babesia microti*, the most common cause for Babesiosis in the United States is wide epidemic in the Northeastern and upper Midwestern states. This species has been implicated in a majority of the transfusion-transmitted Babesiosis (TTB) cases in the United States and is currently the most reported transfusion-transmitted disease to the FDA. Between 2005 and 2010, 3.6% of transfusion-related deaths reported to the FDA were attributed to TTB. However, there is no FDA approved test for blood screening for *Babesia* to date despite the risk that this agent poses to the United States blood supply.

SUMMARY OF THE CLAIMED INVENTION

The invention provides a reagent comprising ammonium chloride, lithium lauryl sulfate (LLS), and an anti-coagulant. In some embodiments, the reagent further comprises a buffer. In some embodiments, the buffer is sodium bicarbonate. In some embodiments, the pH of the buffer is 7-8 or 7.2-7.6. In some embodiments, the anti-coagulant is EDTA, heparin, or citrate.

In some embodiments, the concentration of ammonium chloride in the reagent is 100-500 mM, 200-300 mM, or 250 mM. In some embodiments, the concentration of LLS in the reagent is 4-15% (w/v), 5-8% (w/v), or 5% (w/v). In some embodiments, the concentration of sodium bicarbonate in the reagent is 5-30 mM, 10-20 mM, or 14 mM. In some embodiments, the concentration of ammonium chloride is 250 mM, the concentration of LLS is 5% (w/v), the concentration of sodium bicarbonate is 14 mM, and the pH is 7.2-7.6.

In some embodiments, the reagent is admixed with red blood cells or products derived from red blood cells. In certain embodiments, the reagent is admixed with whole blood. In some embodiments, the reagent is admixed with whole blood in a ratio of 3:1 (v/v). In some embodiments, the whole blood is human whole blood, non-human whole blood, or a mixture thereof.

The invention further provides a method of analyzing a target from red blood cells comprising: (a) contacting red blood cells with a reagent comprising ammonium chloride and an anionic detergent, the reagent being effective to lyse the red blood cells and inhibit degradation of target released from the red blood cells; and (b) analyzing the target released from the red blood cells.

In some methods, the target is a pathogen-derived target. In some methods, the target is RNA.

In some methods, at least 50% of the red blood cells are lysed in five minutes or less. In some methods, the percentage of lysed red blood cells is higher than the percentage of lysed white blood cells.

In some methods, analyzing the target comprises contacting the released target with a capture probe and an immobilized probe, the capture probe having a first segment complementary to the target, and a second segment complementary to the immobilized probe, wherein the target binds to the capture probe, and wherein the bound capture probe binds to the immobilized probe. Some methods further comprise performing a transcription mediated amplification of the target and detecting the resulting amplification product with a detection probe.

Some methods are performed without a centrifugation step to separate the reagent from the target released from the red blood cells.

In some methods, the target is 18S rRNA from a pathogenic organism of the genus *Babesia*. In some methods, the pathogenic organism is of the species *Babesia microti*. In some methods, the limit of detection is at least *Babesia* $2\times10^3$ copies of *Babesia microti* 18S rRNA per 1 mL of whole blood.

BRIEF DESCRIPTION OF THE FIGURES

FIG. 3 shows the compositions of various lysis reagents and their potential use for lysing whole blood samples for detection of *Babesia* 18S rRNA.

BRIEF DESCRIPTION OF THE SEQUENCES

Figure 1:
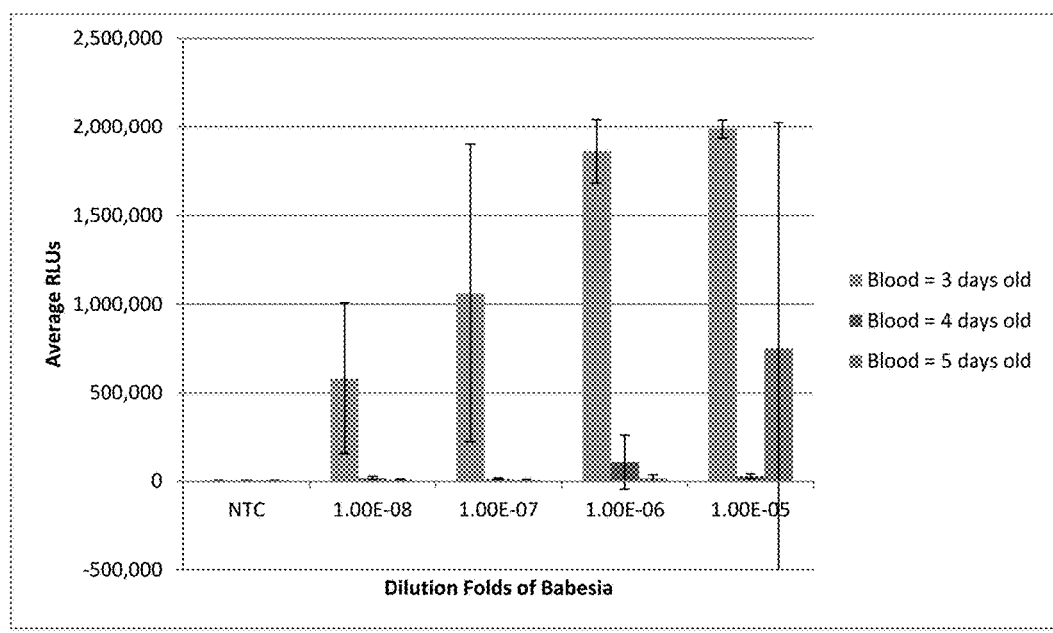
FIG. 1 shows detection of *Babesia* 18S rRNA in human whole blood spiked with *Babesia*-infected hamster blood. Samples were lysed with a lysis reagent of buffered ammonium chloride (ACL) at a concentration of 250 mM. *Babesia* 18S rRNA was detected using Procleix target capture reagent (TCR) and transcription mediated amplification (TMA).

SEQ ID NO:1 sets forth the nucleic acid sequence of a non T7 primer.

SEQ ID NO:2 sets forth the nucleic acid sequence of a T7 primer.

SEQ ID NO:3 sets forth the nucleic acid sequence of an acridinium ester (AE) probe.

SEQ ID NO:4 sets forth the nucleic acid sequence of a target capture oligonucleotide (TCO) probe.

SEQ ID NO:5 sets forth the nucleic acid sequence of an in vitro transcript copy of *Babesia* 18S rRNA.

DEFINITIONS

Pathogens include viruses, bacteria, protozoa, fungi, and other microorganisms responsible for disease in humans and other animals.

A target can be a single type of molecule, such as a protein or 18S rRNA of *Babesia*, or a class of molecules, such as any protein or RNA from *Babesia* or any protein or RNA from red blood cells. Multiple distinct targets can also be analyzed, such as an RNA target and a protein target, or two distinct RNA targets, such as two different mRNA targets, or an mRNA target and an rRNA target. Targets include endogenous components of red blood cells and components arising as a result of pathogenic infection of infected red blood cells and are typically encoded by the infecting pathogen (i.e., "pathogenic" or "pathogen-derived" targets).

A lysis reagent is reagent, often provided in the form of a solution, effective for inducing lysis of red blood cells in whole blood or red blood cell products such as pelleted red blood cells.

Preferential lysis of red blood cells over other cellular components of blood means that the percentage of red blood cells lysed is higher than that of other cellular components present in the sample being analyzed, the other cell types being assessed in the aggregate.

Anionic detergents are compounds with a negatively charged, anionic head group and a long hydrocarbon tail, often provided as a salt with an alkali metal or ammonium ion.

Anti-coagulants inhibit clotting of whole blood. Anti-coagulants include heparins and calcium chelating agents. Heparins activate antithrombin III, which inhibits the activity of thrombin and other proteases involved in blood clotting. Calcium chelating agents, such as EDTA and citrate, bind calcium ions required for blood clotting.

A buffer refers to a weak acid or weak base used to maintain the pH of a solution.

A nucleic acid refers to a multimeric compound comprising nucleotides or analogs that have nitrogenous heterocyclic bases or base analogs linked together to form a polymer, including conventional RNA, DNA, mixed RNA-DNA, and analogs thereof.

The nitrogenous heterocyclic bases can be referred to as nucleobases. Nucleobases can be conventional DNA or RNA bases (A, G, C, T, U), base analogs, e.g., inosine, 5-nitroindazole L-nucleotides, and others (The Biochemistry of the Nucleic Acids 5-36, Adams et al., ed., 11.sup.th ed., 1992; van Aerschott et al., 1995, Nucl. Acids Res. 23(21): 4363-70), imidazole-4-carboxamide (Nair et al., 2001, Nucleosides Nucleotides Nucl. Acids, 20(4-7):735-8), pyrimidine or purine derivatives, e.g., modified pyrimidine base 6H,8H-3,4-dihydropyrimido[4,5-c][1,2]oxazin-7-one (sometimes designated "P" base that binds A or G) and modified purine base N6-methoxy-2,6-diaminopurine (sometimes designated "K" base that binds C or T), hypoxanthine (Hill et al., 1998, Proc. Natl. Acad. Sci. USA 95(8):4258-63, Lin and Brown, 1992, Nucl. Acids Res. 20(19):5149-52), 2-amino-7-deaza-adenine (which pairs with C and T; Okamoto et al., 2002, Bioorg. Med. Chem. Lett. 12(1):97-9), N-4-methyl deoxygaunosine, 4-ethyl-2'-deoxycytidine (Nguyen et al., 1998, Nucl. Acids Res. 26(18):4249-58), 4,6-difluorobenzimidazole and 2,4-difluorobenzene nucleoside analogues (Kiopffer & Engels, 2005, Nucleosides Nucleotides Nucl. Acids, 24(5-7) 651-4), pyrene-functionalized LNA nucleoside analogues (Babu & Wengel, 2001, Chem. Commun. (Camb.) 20: 2114-5; Hrdlicka et al., 2005, J. Am. Chem. Soc. 127(38): 13293-9), deaza- or aza-modified purines and pyrimidines, pyrimidines with substituents at the 5 or 6 position and purines with substituents at the 2, 6 or 8 positions, 2-aminoadenine (nA), 2-thiouracil (sU), 2-amino-6-methylaminopurine, O-6-methylguanine, 4-thio-pyrimidines, 4-amino-pyrimidines, 4-dimethylhydrazine-pyrimidines, and O-4-alkyl-pyrimidines (U.S. Pat. No. 5,378,825; PCT No. WO 93/13121; Gamper et al., 2004, Biochem. 43(31): 10224-36), and hydrophobic nucleobases that form duplex DNA without hydrogen bonding (Berger et al., 2000, Nucl. Acids Res. 28(15): 2911-4). Many derivatized and modified nucleobases or analogues are commercially available (e.g., Glen Research, Sterling, Va.).

A nucleobase unit attached to a sugar, can be referred to as a nucleobase unit, or monomer. Sugar moieties of a nucleic acid can be ribose, deoxyribose, or similar compounds, e.g., with 2' methoxy or 2' halide substitutions. Nucleotides and nucleosides are examples of nucleobase units.

The nucleobase units can be joined by a variety of linkages or conformations, including phosphodiester, phosphorothioate or methylphosphonate linkages, peptide-nucleic acid linkages (PNA; Nielsen et al., 1994, Bioconj. Chem. 5(1): 3-7; PCT No. WO 95/32305), and a locked nucleic acid (LNA) conformation in which nucleotide monomers with a bicyclic furanose unit are locked in an RNA mimicking sugar conformation (Vester et al., 2004, Biochemistry 43(42):13233-41; Hakansson & Wengel, 2001, Bioorg. Med. Chem. Lett. 11 (7):935-8), or combinations of such linkages in a nucleic acid strand. Nucleic acids may include one or more "abasic" residues, i.e., the backbone includes no nitrogenous base for one or more positions (U.S. Pat. No. 5,585,481).

A nucleic acid may include only conventional RNA or DNA sugars, bases and linkages, or may include both conventional components and substitutions (e.g., conventional RNA bases with 2'-O-methyl linkages, or a mixture of conventional bases and analogs). Inclusion of PNA, 2'-methoxy or 2'-fluoro substituted RNA, or structures that affect the overall charge, charge density, or steric associations of a hybridization complex, including oligomers that contain charged linkages (e.g., phosphorothioates) or neutral groups (e.g., methylphosphonates) may affect the stability of duplexes formed by nucleic acids.

An oligomer may contain a "random polymer" sequence that refers to a population of oligomers that are substantially the same in overall length and other characteristics, but in which at least a portion of the oligomer is synthesized by random incorporation of different bases for a specified length, e.g., a random assortment of all four standard bases (A, T, G, and C) in a DNA oligomer, or a random assortment of a few bases (U or T and G) in a defined portion of a larger oligomer. The resulting oligomer is actually a population of oligomers whose finite number of members is determined by the length and number of bases making up the random portion (e.g., $2^6$ oligomers in a population of oligomers that contains a 6-nt random sequence synthesized by using 2 different bases).

Complementarity of nucleic acids means that a nucleotide sequence in one strand of nucleic acid, due to orientation of its nucleobase groups, hydrogen bonds to another sequence on an opposing nucleic acid strand. The complementary bases typically are, in DNA, A with T and C with G, and, in RNA, C with G, and U with A. Complementarity can be perfect (i.e., exact) or substantial/sufficient. Perfect complementarity between two nucleic acids means that the two nucleic acids can form a duplex in which every base in the duplex is bonded to a complementary base by Watson-Crick pairing. "Substantial" or "sufficient" complementary means that a sequence in one strand is not completely and/or perfectly complementary to a sequence in an opposing strand, but that sufficient bonding occurs between bases on the two strands to form a stable hybrid complex in set of hybridization conditions (e.g., salt concentration and temperature). Such conditions can be predicted by using the sequences and standard mathematical calculations to predict the Tm of hybridized strands, or by empirical determination of Tm by using routine methods. Tm refers to the temperature at which a population of hybridization complexes formed between two nucleic acid strands are 50% denatured. At a temperature below the Tm, formation of a hybridization complex is favored, whereas at a temperature above the Tm, melting or separation of the strands in the hybridization complex is favored. Tm may be estimated for a nucleic acid having a known G+C content in an aqueous 1 M NaCl solution by using, e.g., Tm=81.5+0.41(% G+C), although other known Tm computations take into account nucleic acid structural characteristics.

"Separating" or "isolating" or "purifying" refers to removing one or more components from a complex mixture, such as a sample. Preferably, a separating, isolating or purifying step removes at least 70%, preferably at least 90%, and more preferably at least 95% w/w of the target nucleic acids from other sample components. A separating, isolating or purifying step may optionally include additional washing steps to remove non-target sample components.

"Release" of a capture hybrid refers to separating one or more components of a capture hybrid from each other, such as separating a target nucleic acid from a capture probe, and/or a capture probe from an immobilized probe. Release of the target nucleic acid strand separates the target from other components of a capture hybrid and makes the target available for binding to a detection probe. Other components of the capture hybrid may remain bound, e.g., the capture probe strand to the immobilized probe on a capture support, without affecting target detection.

A "label" refers to a molecular moiety that is detectable or produces a detectable response or signal directly or indirectly, e.g., by catalyzing a reaction that produces a detectable signal. Labels include luminescent moieties (such as fluorescent, bioluminescent, or chemiluminescent compounds), radioisotopes, members of specific binding pairs (e.g., biotin and avidin), enzyme or enzyme substrate, reactive groups, or chromophores, such as a dye or particle that results in detectable color.

A capture probe includes a first segment including a target-complementary region of sequence and a second segment for attaching the capture probe, or a hybridization complex that includes the capture probe, to an immobilized probe. The first segment can be configured to substantially complementary to a specific target nucleic acid sequence so that a first segment and a target nucleic acid can hybridize to form a stable duplex (i.e., having a detectable melting point) under hybridizing conditions, such as described in the Examples. Alternatively, the first segment can be configured to nonspecifically bind to nucleic acid sequences in a sample under hybridizing conditions (see WO 2008/016988). The second segment includes a region of sequence that is complementary to a sequence of an immobilized probe. Preferably, a chimeric capture probe includes a nucleic acid homopolymer (e.g., poly-A or poly-T) that is covalently attached to the target-complementary region of the capture probe and that hybridizes under appropriate conditions to a complementary homopolymer of the immobilized probe (e.g., poly-T or poly-A, respectively) as previously described (U.S. Pat. No. 6,110,678 to Weisburg et al.). Capture probes may further comprise a third segment that acts as a closing sequence to inactivate unbound target capture probes in a capture reaction. This third segment can flank the first segment opposite the second segment (e.g., capture sequence:target hybridizing sequence:closing sequence) or it can flank the second segment opposite the first segment (e.g., closing sequence:capture sequence:target hybridizing sequence). See WO 2006/007567 and US 2009-0286249.

An immobilized probe includes a nucleic acid joined directly or indirectly to a support. The nucleic acid is complementary to a nucleic acid in the capture probe, although may or may not be the same length (number of nucleobase units) as the in the capture probe. The nucleic acid in the immobilized probe preferably contains at least six contiguous nucleobase units and can contain for example 10-45 or 10-40 or 10-30 or 10-25 or 15-25, inclusively, L-nucleobase units. The nucleic acid is preferably a homopolymer, and more preferably a homopolymer of adenine or thymine. A preferred form of immobilized probe is or includes a homopolymer of 14 thymine residues for use in combination with a capture probe including a second segment with a homopolymer of adenine residues. The nucleic acid moiety of an immobilized probe is typically provided in single-stranded form, or if not, is denatured to single-stranded form before or during use.

Any of a variety of materials may be used as a support for the immobilized probes, e.g., matrices or particles made of nitrocellulose, nylon, glass, polyacrylate, mixed polymers, polystyrene, silane polypropylene, and magnetically attractable materials. Monodisperse magnetic spheres are a preferred support because they are relatively uniform in size and readily retrieved from solution by applying a magnetic force to the reaction container, preferably in an automated system. An immobilized probe may be linked directly to the capture support, e.g., by using any of a variety of covalent linkages, chelation, or ionic interaction, or may be linked indirectly via one or more linkers joined to the support. The linker can include one or more nucleotides not intended to hybridize to the capture probe but to act as a spacer between the nucleic acid of the immobilized probe and its support.

A "detection probe" is a nucleic acid or other molecule that binds specifically to a target sequence and which binding results, directly or indirectly, in a detectable signal to indicate the presence of the target sequence. A detection probe need not be labeled to produce a detectable signal, e.g., an electrical impulse resulting from binding the probe to its target sequence may be the detectable signal. A "labeled probe" is a probe that contains or is linked, directly or indirectly, to a label (e.g., Sambrook et al., Molecular Cloning, A Laboratory Manual, 2nd ed., Chapt. 10; U.S. Pat. No. 6,361,945, Becker et al.; U.S. Pat. No. 5,658,737, Nelson et al.; U.S. Pat. No. 5,656,207, Woodhead et al.; U.S. Pat. No. 5,547,842, Hogan et al.; U.S. Pat. No. 5,283,174, Arnold et al.; U.S. Pat. No. 4,581,333, Kourilsky et al.; U.S. Pat. No. 5,731,148, Becker et al.). For example, detection probes may include a non-nucleotide linker and a chemiluminescent label attached to the linker (U.S. Pat. Nos. 5,185,439, 5,585,481 and 5,639,604, Arnold et al.). Examples of detection probes include oligonucleotides of about 5 to 50 nucleotides in length having an attached label that is detected in a homogeneous reaction, e.g., one that uses differential hydrolysis of a label on a bound or unbound probe.

Detection probes can have a nucleotide sequence that is of the same or opposite sense as a target sequence depending on the format of the assay. Detection probes can hybridize to the same or different segment of a target sequence as a capture probe. Some detection probes have an attached chemiluminescent marker, e.g., an acridinium ester (AE) compound (U.S. Pat. Nos. 5,185,439, 5,639,604, 5,585,481, and 5,656,744). In some detection probes, an acridinium ester label is attached to a central region of the probe near a region of A and T base pairs by using a non-nucleotide linker (U.S. Pat. Nos. 5,585,481 and 5,656,744, Arnold, et al.) which restricts the amines of the nucleotide bases on both sides of the AE and provides a site for intercalation. Alternatively, an AE label may be attached to the 3' or 5' terminus of the detection probe which is used in conjunction with a second oligomer that hybridizes adjacent to the detection probe on the target nucleic acid to restrict the effects of nearby amine contributed by the target nucleic acid. In some detection probes, an AE label at or near the site of a mismatch with a related non-target polynucleotide sequence, to permit discrimination between the related sequence and the target sequence that may differ by only one nucleotide because the area of the duplex around the mismatch site is sufficiently destabilized to render the AE on the probe hybridized to the related non-target sequence susceptible to hydrolysis degradation. HIV-1 and HCV may be detected using a modified form of the commercial PROCLEIX® ULTRIO HIV-1/HCV/HBV Assay from Gen-Probe. The modification involves replacing the D-polyA and D-polyT sequences in capture and immobilized probes with L-poly A and L-poly-T, respectively.

"Hybridization condition" refers to the cumulative environment in which one nucleic acid strand bonds to a second nucleic acid strand by complementary strand interactions and hydrogen bonding to produce a hybridization complex. Such conditions include the chemical components and their concentrations (e.g., salts, chelating agents, formamide) of an aqueous or organic solution containing the nucleic acids, and the temperature of the mixture. Other factors, such as the length of incubation time or reaction chamber dimensions may contribute to the environment (e.g., Sambrook et al., Molecular Cloning, A Laboratory Manual, 2.sup.nd ed., pp. 1.90-1.91, 9.47-9.51, 11.47-11.57 (Cold Spring Harbor Laboratory Press, Cold Spring Harbor, N. Y., 1989)).

Specific binding of a target capture oligomer to a target nucleic or target nucleic acids means binding between a single defined sequence in the first segment of a target capture oligomer and an exactly or substantially complementary segment on target nucleic acid(s) to form a stable duplex. Such binding is detectably stronger (higher signal or melting temperature) than binding to other nucleic acids in the sample lacking a segment exactly or substantially complementary to the single defined target capture oligomer sequence. Non-specific binding of a target capture oligomer to target nucleic acids means that the target capture oligomer can bind to a population of target sequences that do not share a segment having exact or substantial complementarity to a single defined target capture oligomer sequence. Such can be achieved by for example using a randomized sequence in the first segment of the capture probe.

Lack of binding between nucleic acids can be manifested by binding indistinguishable from nonspecific binding occurring between a randomly selected pair of nucleic acids lacking substantial complementarity but of the same lengths as the nucleic acids in question.

"Release" of a capture hybrid refers to separating one or more components of a capture hybrid from each other, such as separating a target nucleic acid from a capture probe, and/or a target capture oligomer from an immobilized probe. Release of the target nucleic acid strand separates the target from other components of a capture hybrid and makes the target available for binding to a detection probe. Other components of the capture hybrid may remain bound, e.g., the target capture oligomer strand to the immobilized probe on a capture support, without affecting target detection.

"Sensitivity" is the proportion of true positives correctly identified as such (e.g. the percentage of infected patients correctly identified as having the infection). Specificity measures the proportion of true negatives which are correctly identified (e.g. the percentage of uninfected patients who are correctly identified as not having the infection.)

Reference to a range of values also includes integers within the range and sub-ranges defined by integers in the range. Reference to any numerical value or range of numerical values should be understand as encompassing any such variation as is inherent in measuring that value other typical conditions of use.

DETAILED DESCRIPTION

I. General

The invention provides a lysis reagent for lysing red blood cells, thereby releasing RNA or other target in a form suitable for analysis. The lysis reagent includes at least ammonium chloride and an anionic detergent, and may include an anti-coagulant. The reagent serves to lyse red blood cells, protect a released target from degradation in the lysate, and is compatible with subsequent steps for analysis of the target, such as target capture, amplification, detection, and/or sequencing. Preferably, the lysis reagent preferentially lyses red blood cells in a sample (e.g., whole blood) relative to white blood cells or other cells present to reduce contamination from lysates of other cells types and produce a homogeneous sample. The lysis reagent is particularly amenable for analysis of RNA from pathogens infecting red blood cells, including parasitic organisms such as *Babesia* and *Plasmodium* species.

The invention results in part from identifying deficiencies with various known lysis agents for preparing and analyzing pathogen-derived RNA from red blood cells. Known lysis agents were found to be incompatible with reagents and methods for analyzing pathogen-derived RNA, causing cell clumping, the appearance of precipitate, and the loss of magnetic beads when lysed samples were added to capture reagents. By contrast, the present lysis reagent was compatible with these methods, allowing for the preferential lysis of red blood cells in whole blood samples and the sensitive detection of the released pathogen-derived RNA following target capture and transcription mediated amplification. The present lysis reagent also inhibited degradation of the pathogen-derived RNA by nucleases and proteases following lysis and demonstrated reproducibility between samples.

II. Lysis Reagents

The present lysis reagent includes at least ammonium chloride and an anionic detergent, and preferably an anti-coagulant. Ammonium chloride (ACL) acts as a lysing agent. In whole blood, ammonium chloride preferentially lyses red blood cells over white blood cells, thus reducing contamination of the sample and interference with steps of the detection assay. Exemplary concentration ranges for ammonium chloride include 100-1000 mM, 100-800 mM, 100-500 mM, 150-300 mM, 200-300 mM, 240-260 mM, or 250 mM.

The anionic detergent can act as both a lysing agent and as an inhibitor of target degradation following the lysis of red blood cells. The anionic detergent is particularly useful for inhibiting the degradation of nucleic acids. Exemplary anionic detergents include lithium lauryl sulfate (LLS) or sodium dodecyl sulfate (SDS). LLS is preferred. By way of example, a concentration range of 147 mM to 550 mM for LLS are 4-15% (w/v), 5-8% (w/v), or about 5% (w/v) of a stock LLS solution.

The anti-coagulant, if present, is used at a concentration sufficient to inhibit clotting of the sample (e.g., whole blood or red blood cells). By inhibiting clotting, the anti-coagulant eliminates the need to centrifuge samples during the method to isolate red blood cells. Exemplary anti-coagulants include EDTA, heparin, or citrate. EDTA is preferred. Exemplary concentrations of EDTA include 0.01-10 mM, 0.05-1.0 mM, 0.05-0.50 mM, 0.075-0.125 mM, or 0.1 mM.

The lysis reagent can also include a buffer. Sodium bicarbonate is one example of a suitable buffer. Others suitable buffers are ACES, PIPES, MPSO, imidazole, Tris, BES, MOPS, HEPES, TES, MOBS, DIPSO, TAPSO, triethanolamine, pyrophosphate, HEPPSO, and POPSO. Sodium bicarbonate or other buffer can be present in the reagent at a concentration of, for example 5-30 mM, 10-20 mM, 12-16 mM or 14 mM. The pH of the buffer used in the reagent can be, for example, 7-8, or 7.2-7.6.

A preferred lysis reagent includes ammonium chloride, LLS, EDTA and sodium bicarbonate in a powder form or in a solvent, such as water, at any of the concentrations indicated above. Preferably ammonium chloride is at a concentration of 100-500 mM or 250 mM, LLS at a concentration of 4-15% or 5% (w/v), EDTA at a concentration of 0.01-10 mM or 0.1 mM, and sodium bicarbonate at a concentration of 12-16 mM or 14 mM, with a pH of 7.2-7.6. Optionally, the lysis reagent consists essentially of ammonium chloride, LLS, EDTA, sodium bicarbonate and water.

The lysis reagent can be provided as a kit also including probe and or primers for performing an assay on a target to be isolated from red blood cells, including any of the targets described below. Such a kit can include instructions for using the lysis reagent and/or performing an assay on a target isolated from red blood cells.

III. Use of Lysis Reagents

Red blood cells can be obtained from any available source, such as whole blood or any fraction thereof that includes red blood cells, such as pelleted red blood cells. Whole blood can be human whole blood, non-human whole blood, or a combination thereof.

The lysis reagent can be admixed with red blood cells for a time sufficient to induce cell lysis and cause release of molecules of desired target(s) from cells. Exemplary times for maintaining red blood cells admixed with lysis reagent include 1-30 minutes, 2-15 minutes, 3-10 minutes, 4-6 minutes, or 5 minutes. Preferably, the time is no more than 30, 15, 10 or 5 minutes. Preferably the mixture lacks visible particles after lysis.

The temperature of incubation of the lysis reagent with red blood cells can vary. The temperature is preferably chosen to maximize extent and rate of lysis and preference for red blood cells over white blood cells or other cells in the sample and to minimize degradation of target(s) or prevent inhibition of subsequent processing. Exemplary temperature ranges include 0-50° C., 5-45° C., 10-40° C., 15-37° C., 20-30° C., 22-27° C., or 25° C. Ambient temperature is suitable. Lysis of red blood cells should release a sufficient amount of target molecules to be detectable by the methods described herein. Preferably lysis results in at least 50%, 60%, 70%, 80%, 90%, or 100% lysis of red blood cells in a sample being lysed.

The ratio at which whole blood is combined with lysis reagent can affect the extent and rate of cell lysis and protection of target molecules from degradation after release from lysed cells. Exemplary ratios in which whole blood is admixed with the lysis reagent include ratios of 1:1, 1:2, 1:3, 1:4, 1:5, 1:10, or in a range of ratios between 1:1 and 1:10 (v/v; whole blood:reagent). A preferred ratio is whole blood admixed with the lysis reagent at a ratio of about 1:3 (v/v). When the sample comprises red blood cells isolated from whole blood, such as pelleted red blood cells, the red blood cells can be admixed with the lysis reagent at exemplary ratios of 1:1, 1:2, 1:3, 1:4, 1:5, 1:10, or in a range of ratios between 1:1 and 1:10 (v/v; red blood cells:reagent).

IV. Targets

Targets released from red blood cells by the present lysis reagent can include endogenous or pathogenic nucleic acids (e.g., DNA or RNA), whole particles, proteins from pathogenic viruses or organisms, and/or antibodies, lipids and carbohydrates. Pathogen-derived RNA targets are preferred. Various types of RNA can be detected. The RNA can be ribosomal RNA (rRNA), messenger RNA (mRNA), or heterogeneous nuclear RNA (hnRNA). A preferred target for pathogens is ribosomal RNA, particularly 18S rRNA, 5S rRNA, 5.8S rRNA, or 28S rRNA.

Exemplary pathogenic organisms include parasites from the genus *Babesia, Plasmodium, Trypanosoma, Leishmania, Anaplasma*, or *Toxoplasma*. Organisms of the genus *Babesia* that cause disease in humans can be *Babesia microti, Babesia divergens*, or *Babesia duncani*. Organisms of the genus *Plasmodium* can be *Plasmodium falciparum, Plasmodium malariae, Plasmodium ovale, Plasmodium vivax*, or *Plasmodium knowlesi*.

V. Assays

Target molecules released from lysis of red blood cells are subject to analysis. Target molecules may or may not be separated from the lysis reagent (by centrifugation or otherwise) before analysis. Omission of a separation step can facilitate efficient work flow in performing the assay. The type of assay depends on the target.

A. Nucleic Acids

Analysis of nucleic acid targets often involves steps of capture, amplification and detection. Alternatively, amplification and detection methods can be performed without prior target capture. Preferably amplification, and detection and target capture (if performed) occur without separation of target molecules from the lysis reagent. Thus, the entire process can be performed in a single vessel.

1. Target Capture Assay

An exemplary target capture assay can be performed as follows using one or more capture probes, an immobilized probe, a sample, and a suitable medium to permit hybridization of the target capture oligomer to the target nucleic acid and of target capture oligomer to the immobilized probe. The target sample can be heated (e.g., from 65° C. to 95° C.) before performing the assay to denature any nucleic acids in double-stranded form. The components can be mixed in any order. For example the target capture oligomer can be added to the sample and hybridized with the target nucleic acid in the sample before adding the immobilized probe. However, for an automated assay, it is preferable to minimize the number of adding steps by supplying the target capture oligomer and immobilized probe at the same or substantially the same time. In this case, the order of hybridization can be controlled by performing a first hybridization under conditions in which a duplex can form between the target capture oligomer and the target nucleic acid but which exceeds the melting temperature of the duplex that would form between first and second stem segments of the capture probe and between the target capture oligomer and immobilized probe, and then performing a second hybridization under conditions of reduced stringency, preferably below the melting temperature of the duplexes formed between the first and second stem segments and between the target capture oligomer and the immobilized probe. Stringency can be reduced by lowering the temperature of the assay mix. At the higher temperature, the target binding site duplexes with the target nucleic acid. At the lower temperature, the first and second stem segments of capture probes not bound to the target nucleic acid duplex with one another and the first stem segment of capture probes bound to the target nucleic acid duplexes with the immobilized probe. For example, the higher stringency hybridization can be performed at or around 60° C. and the lower stringency hybridization by allowing cooling to room temperature or 25° C. Stringency can also be reduced by reducing salt concentration or adding or increasing concentration of a chaotropic solvent. In some methods, all steps (with the possible exception of an initial denaturation step at higher temperature to denature double stranded target) can be performed isothermally.

Following formation of the target nucleic acid:capture probe, immobilized probe hybrid (the capture hybrid complex) is separated away from other sample components by physically separating the capture support using any of a variety of known methods, e.g., centrifugation, filtration, or magnetic attraction of a magnetic capture support. The separation is preferably performed at a temperature below the melting temperature of stem-loop structures formed by target capture oligomers so that empty target capture oligomers have no opportunity to denature and thus bind to the capture probe. In some methods, the separation is performed at a temperature less than but within 10° C. of the melting temperature of the stem-loop structure (e.g., at 60° C.) to maintain stringency of hybridization conditions and consequent ability to distinguished matched and unmatched target nucleic acids.

To further facilitate isolation of the target nucleic acid from other sample components that adhere non-specifically to any portion of the capture hybrid, the capture hybrid may be washed one or more times to dilute and remove other sample components. Washing may be accomplished by dissociating the capture hybrid into its individual components in an appropriate aqueous solution (e.g., a solution containing Tris and EDTA. See e.g., U.S. Pat. No. 6,110,678) and appropriate conditions (e.g., temperature above the $T_m$ of the components) and then readjusting the conditions to permit reformation of the capture hybrid. However, for ease of handling and minimization of steps, washing preferably rinses the intact capture hybrid attached to the capture support in a solution by using conditions that maintain the capture hybrid. Preferably, capture of the target nucleic acid with washing if performed, isolates at least 70%, preferably at least 90%, and more preferably about 95% of the target nucleic acids away from other sample components. Isolated nucleic acids can be used for a number of downstream processes, such as nucleic acid amplification.

A target capture assay may also be performed as part of a real-time, biphasic, target capture and amplification method. In such a method, 500 µL of sample and 400 µL of target capture reagent (TCR) are added to reaction tubes. The TCR contains magnetic particles, components to lyse organisms present in the sample, capture oligos, a T7 initiation promoter, and an internal calibrator. Fluid in the reaction tubes is mixed for a specific time and speed to ensure the mixture is homogeneous. Reaction tubes are then transferred to a transition incubator at 43.7° C. to preheat the fluid in the reaction tubes. Reaction tubes are then transferred to an anneal incubator set at 64° C. During incubation at 64° C., any organisms present in the sample that were not previously disrupted by the lysis reagent are disrupted, causing release of the target. Reaction tubes are then moved to a transition incubator to start a cool down process, and are further cooled in a chiller ramp (17° C. to 19° C.), leading to binding of the T7 initiation promoter and capture of both the target and the internal calibrator to the magnetic particles via the capture oligos. The reaction tubes are moved to a magnetic parking station where they are subjected to magnets which pull the magnetic particles to the sides of the tubes prior to entering a wash station. In the wash station, potential interfering substances are removed from the reaction by washing the magnetic particles.

2. Amplification

A nucleic acid target can be amplified using methods such as transcription mediated amplification (TMA), polymerase chain reaction (PCR), Nucleic Acid Sequence-Based Amplification, ligase chain reaction or other amplification methods. Detection of the amplified target RNA products can be performed during amplification (real-time) or following amplification (end-point).

i. Transcription Mediated Amplification

TMA has been previously described (e.g., U.S. Pat. Nos. 5,399,491, 5,554,516, 5,824,518 and 7,833,716; and also e.g., F. Gonzales and S. McDonough. Applications of Transcription-Mediated Amplification to Quantification of Gene Sequences. Gene Amplification. 1998 Ed. Francois Ferre, Birkhauser, Boston. PP. 189-204). In TMA, a target nucleic acid that contains the sequence to be amplified is provided as single stranded nucleic acid (e.g., ssRNA or ssDNA). Any conventional method of converting a double stranded nucleic acid (e.g., dsDNA) to a single-stranded nucleic acid may be used. A promoter primer binds specifically to the target nucleic acid at its target sequence and a reverse transcriptase (RT) extends the 3' end of the promoter primer using the target strand as a template to create a cDNA copy, resulting in a RNA:cDNA duplex. RNase activity (e.g., RNase H of RT enzyme) digests the RNA of the RNA:cDNA duplex and a second primer binds specifically to its target sequence in the cDNA, downstream from the promoter-primer end. Then RT synthesizes a new DNA strand by extending the 3' end of the second primer using the cDNA as a template to create a dsDNA that contains a functional promoter sequence. RNA polymerase specific for the functional promoter initiates transcription to produce about 100 to 1000 RNA transcripts (amplified copies or amplicons) complementary to the initial target strand. The second primer binds specifically to its target sequence in each amplicon and RT creates a cDNA from the amplicon RNA template to produce a RNA:cDNA duplex. RNase digests the amplicon RNA from the RNA:cDNA duplex and the target-specific sequence of the promoter primer binds to its complementary sequence in the newly synthesized DNA and RT extends the 3' end of the promoter primer as well as the 3' end of the cDNA to create a dsDNA that contains a functional promoter to which the RNA polymerase binds and transcribes additional amplicons that are complementary to the target strand. Autocatalytic cycles that use these steps repeatedly during the reaction produce about a billion-fold amplification of the initial target sequence. Optionally, amplicons may be detected during amplification (real-time detection) or at an end point of the reaction (end-point detection) by using a probe that binds specifically to a sequence contained in the amplicons. Detection of a signal resulting from the bound probes indicates the presence of the target nucleic acid in the sample.

TMA may also be performed as part of a real-time, biphasic, target capture and amplification method. In such a method, TMA can be performed by adding amplification reagent (50 μL/test) to reaction tubes containing captured target molecules and mixing in an amplification load station. The amplification reagent contains oligos and components necessary to build nucleic acids. The reaction tubes are moved to a transition incubator at 43.7° C. to increase the temperature of the liquid in the reaction tubes, which are then moved back to the amplification load station where enzyme (25 μL/test) is added. Reaction tubes are moved to the amplification incubator set at 42.7° C. and remain in the incubator for five minutes, during which the first rounds of amplification are initiated. Reaction tubes are moved back to the amplification load station where promoter reagent (25 μL/test) is added. Reaction tubes are moved back to the amplification incubator for further rounds of target amplification. The promoter reagent contains oligos and torches. The torches are complementary to the target or internal calibrator and fluoresce when bound, generating signal in real-time. The signals for the target and internal calibrator preferably have different wavelengths and can be distinguished.

ii. Polymerase Chain Reaction

Alternatively, PCR amplification (e.g., reverse transcriptase or real-time PCR) can be used for amplification. PCR can be performed with or without prior release of the target nucleic acid from the capture complex. The PCR reaction can be performed in the same vessel (e.g., a microfuge tube) as the capture step. The PCR reaction involves thermocycling between a high temperature of about 95° C. (e.g., 90-99° C.) for dissociation and a low temperature of about 60° C. e.g., 40-75, or 50-70 or 55-64° C.) for annealing. Typically, the number of complete thermocycles is at least 10, 20, 30 or 40. PCR amplification is performed using one or more primer pairs. A primer pair used for PCR amplification includes two primers complementary to opposite strands of a target nucleic acid flanking the region desired to be sequenced. For sequencing most of a viral genome (e.g., more than 50, 75 or 99%), the primers are preferably located close to the ends of the viral genome. For amplification of related molecules (e.g., mutant forms of the same virus present in a patient sample), the primers are preferably complementary to conserved regions of the target nucleic acid likely to be present in most members of the population. PCR amplification is described in PCR Technology: Principles and Applications for DNA Amplification (ed. H. A. Erlich, Freeman Press, NY, N.Y., 1992); PCR Protocols: A Guide to Methods and Applications (eds. Innis, et al., Academic Press, San Diego, Calif., 1990); Mattila et al., Nucleic Acids Res. 19, 4967 (1991); Eckert et al., PCR Methods and Applications 1, 17 (1991); PCR (eds. McPherson et al., IRL Press, Oxford); and U.S. Pat. No. 4,683,202.

3. Detection

Detection of a nucleic acid target can be performed following capture and either during (real-time) or following (end-point) amplification by using any known method. The amplification product of RNA is often in the form of DNA resulting from RT-PCR or RNA copies resulting from TMA. Amplified nucleic acids may be detected in solution phase or by concentrating them in or on a matrix and detecting labels associated with them (e.g., an intercalating agent such as ethidium bromide). Some detection methods use probes complementary to a sequence in the amplified product and detect the presence of the probe:product complex, or use a complex of probes to amplify the signal detected from amplified products (e.g., U.S. Pat. Nos. 5,424,413, 5,451, 503 and 5,849,481). Other detection methods use a probe in which signal production is linked to the presence of the target sequence because a change in signal results only when the labeled probe binds to amplified product, such as in a molecular beacon, molecular torch, or hybridization switch probe (e.g., U.S. Pat. Nos. 5,118,801, 5,210,015, 5,312,728, 5,538,848, 5,541,308, 5,656,207, 5,658,737, 5,925,517, 6,150,097, 6,361,945, 6,534,274, 6,835,542, and 6,849,412; and U.S. Pub. No. 2006/0194240 A1). Such probes typically use a label (e.g., fluorophore) attached to one end of the probe and an interacting compound (e.g., quencher) attached to another location of the probe to inhibit signal production from the label when the probe is in one conformation ("closed") that indicates it is not hybridized to amplified product, but a detectable signal is produced when the probe is hybridized to the amplified product which changes its conformation (to "open"). Detection of a signal from directly or indirectly labeled probes that specifically associate with the amplified product indicates the presence of the target nucleic acid that was amplified.

4. Sequencing

Following amplification, a target nucleic acid as well as or instead of undergoing qualitative or quantitative detection can be sequenced. Purification if desired can be performed on a silica column (e.g., a Qiagen gravity flow column). The target nucleic acid binds to the column, where it can be washed and then eluted. Alternatively, purification can be performed using a nucleic acid probe-based purification system (e.g., U.S. Pat. No. 6,110,678 or 8,034,554, US 2013/0209992 or US 2009/0286249, or. WO 2012/037531 or WO 2013/116774). The amplified target DNA can also be adapted for some sequencing formats by attachment of an adapter. The amplified DNA can be tailed by Klenow-mediated addition of nucleotides (usually a homopolymer) followed by annealing to an oligonucleotide complementary to the added tail, and ligation. Depending on the sequencing platform used, special adaptors are ligated to the template before sequencing. For example, a SMRT bell adapter is ligated to the sample template for sequencing with a Pacific Biosciences' PacBio RS sequencer (see, e.g., Travers et al. Nucl. Acids Res. (2010) 38 (15): e159).

The amplified target nucleic acid is suitable for sequence analysis by a variety of techniques. The capture of target nucleic acid can be coupled to several different formats of so-called next generation and third generation sequencing methods. Such methods can sequence millions of target templates in parallel. Such methods are particularly useful when the target nucleic acid is a heterogeneous mixture of variants. Among the many advantages, sequencing variants in parallel provides a profile of drug resistant mutations in the sample, even drug mutations present in relatively minor proportions within the sample.

Some next generation sequence methods amplify by emulsion PCR. A target nucleic acid immobilized to beads via a target capture oligomer provides a suitable starting material for emulsion PCR. The beads are mixed with PCR reagents and emulsion oil to create individual micro reactors containing single beads (Margulies et al., Nature 437, 376-80 (2005)). The emulsion is then broken and the individual beads with amplified DNA are sequenced. The sequencing can be pyrosequencing performed for example using a Roche 454 GS FLX sequencer (454 Life Sciences, Branford, Conn. 06405). Alternatively, sequencing can be ligation/detection performed for example using an ABI SOLiD Sequencing System (Life Technologies, Carlsbad, Calif. 92008). In another variation, target nucleic acids are eluted from beads having target capture oligomers and are immobilized in different locations on an array (e.g., the HiScanSQ (Illumina, San Diego, Calif. 92121)). The target nucleic acids are amplified by bridge amplification and sequenced by template directed incorporation of labeled nucleotides, in an array format (Illumina). In another approach, target nucleic acids are eluted from the target capture oligomer and single molecules are analyzed by detecting in real-time the incorporation nucleotides by a polymerase (single molecule real time sequencing or SMRT sequencing). The nucleotides can be labeled nucleotides that release a signal when incorporated (e.g., Pacific Biosciences, Eid et al., Sciences 323 pp. 133-138 (2009) or unlabeled nucleotides, wherein the system measures a chemical change on incorporation (e.g., Ion Torrent Personal Genome Machine (Life Technologies)).

Although captured target nucleic acids can be sequenced by any technique, third generation, next generation or massively parallel methods offer considerable advantages over Sanger and Maxam Gilbert sequencing. Several groups have described an ultrahigh-throughput DNA sequencing procedure (see. e.g., Cheeseman, U.S. Pat. No. 5,302,509, Metzker et al., Nucleic Acids Res. 22: 4259 (1994)). The pyrosequencing approach that employs four natural nucleotides (comprising a base of adenine (A), cytosine (C), guanine (G), or thymine (T)) and several other enzymes for sequencing DNA by synthesis is now widely used for mutation detection (Ronaghi, Science 281, 363 (1998); Binladin et al., PLoS ONE, issue 2, e197 (February 2007); Rehman et al., American Journal of Human Genetics, 86, 378 (March 2010); Lind et al., Next Generation Sequencing: The solution for high-resolution, unambiguous human leukocyte antigen typing, Hum. Immunol. (2010), doi 10.1016/jhumimm.2010.06.016 (in press); Shafer et al., J Infect Dis. 1; 199(5):610 (2009)). In this approach, the detection is based on the pyrophosphate (PPi) released during the DNA polymerase reaction, the quantitative conversion of pyrophosphate to adenosine triphosphate (ATP) by sulfurylase, and the subsequent production of visible light by firefly luciferase. More recent work performs DNA sequencing by a synthesis method mostly focused on a photocleavable chemical moiety that is linked to a fluorescent dye to cap the 3'-OH group of deoxynucleoside triphosphates (dNTPs) (Welch et al. Nucleosides and Nucleotides 18, 197 (1999) & European Journal, 5:951-960 (1999); Xu et al., U.S. Pat. No. 7,777,013; Williams et al., U.S. Pat. No. 7,645,596; Kao et al, U.S. Pat. No. 6,399,335; Nelson et al., U.S. Pat. Nos. 7,052,839 & 7,033,762; Kumar et al., U.S. Pat. No. 7,041, 812; Sood et al, US Pat. App. No. 2004-0152119; Eid et al., Science 323, 133 (2009)). In sequencing-by-synthesis methodology, DNA sequences are being deduced by measuring pyrophosphate release on testing DNA/polymerase complexes with each deoxyribonucleotide triphosphate (dNTP) separately and sequentially. See Ronaghi et al., Science 281: 363 365 (1998); Hyman, Anal. Biochem. 174, 423 (1988); Harris, U.S. Pat. No. 7,767,400.

B. Other Targets

Antibodies, proteins, particles and other targets can be detected by formats such as immunoprecipitation, Western blotting, ELISA, radioimmunoassay, competitive and immunometric assays. See Harlow & Lane, Antibodies: A Laboratory Manual (CSHP NY, 1988); U.S. Pat. Nos. 3,791, 932; 3,839,153; 3,850,752; 3,879,262; 4,034,074, 3,791, 932; 3,817,837; 3,839,153; 3,850,752; 3,850,578; 3,853, 987; 3,867,517; 3,879,262; 3,901,654; 3,935,074; 3,984, 533; 3,996,345; 4,034,074; and 4,098,876. Sandwich assays are a preferred format (see U.S. Pat. Nos. 4,376,110, 4,486, 530, 5,914,241, and 5,965,375).

Competitive assays can also be used. In some methods, target antigen in a sample competes with exogenously supplied labeled target antigen for binding to an antibody detection reagent. The amount of labeled target antigen bound to the antibody is inversely proportional to the amount of target antigen in the sample. The antibody can be immobilized to facilitate separation of the bound complex from the sample prior to detection.

Lateral flow devices can also be used for detecting a target. Fluid is applied to a test strip that has been treated with a sample in which a target may be present. Labelled binding molecules pass through the strip and can be captured as they pass into a specific zone containing the sample with the target.

VI. Sensitivity

The present methods can provide a high sensitivity of detection of a target from red blood cells. For pathogen-derived RNA targets, sensitivity can be expressed as a minimum number of pathogenic RNA copies present in a volume of whole blood. The volume of whole blood can be that contacted with lysis reagent directly, or can be that used to prepare a blood fraction, such as pelleted red cells, which are in turn contacted with the lysis reagent. Preferably the methods detect the presence of pathogenic RNA in whole blood with a sensitivity of $2\times10^3$ copies of RNA equivalent to one parasite/1 mL of whole blood or better, $2\times10^3$ copies/5 mL of whole blood or better, $2\times10^3$ copies/10 mL of whole blood or better, $2\times10^3$ copies/50 mL of whole blood or better, or $2\times10^3$ copies/100 mL of whole blood or better. In some methods, the range of pathogenic RNA in lysed samples varies between $2\times10^3$ to $2\times10^7$ copies/1 mL of a sample.

EXAMPLES

Example 1

Analysis of Reagents for Cell Lysis and Stabilization of Babesia RNA

The purpose of this example was to identify a lysis reagent that would effectively lyse red blood cells in human whole blood, stabilize Babesia-derived rRNA in the lysed sample, and inhibit the activity of RNAses. To be compatible with Gen-Probe's Target Capture Technology using magnetic beads, the lysis reagent should preferably result in a homogeneous lysate for efficient target capture.

The PAXGENE™ Blood RNA System (BD Biosciences) was first evaluated for Babesia sample preparation. The PAXGENE reagent contained in each tube comprises the active compound tetradecyltrimethylammonium oxalate (TDTMAO), a quaternary ammonium salt known to lyse cell membranes and act as a stabilizing reagent.

The sample used for preparation was human whole blood spiked with Babesia-infected hamster blood at a dilution ranging from $1\times10^{-1}$ to $1\times10^{-6}$. The blood sample (1 mL) was added to 3 mL of lysis reagent from a PAXGENE tube at room temperature and allowed to rock for 5 minutes to induce cell lysis. 500 µL of the lysed sample was then added to 500 µL of a Target Capture Reagent (TCR). Gen-Probe, Procleix, and Aptima TCRs were evaluated. Following addition of the lysed sample to the TCR, a white precipitate formed. Therefore, the PAXGENE system was unsuitable for whole blood lysis and detection of Babesia using Gen-Probe's target capture reagents.

In a next experiment, a lysis reagent of 250 mM ammonium chloride (ACL), buffered with 14 mM sodium bicarbonate, was evaluated. Human whole blood was spiked with Babesia-infected hamster blood at a dilution ranging from $1\times10^{-5}$ to $1\times10^{-8}$. One mL of spiked whole blood was admixed with 3 mL of buffered ACL solution for 5 minutes at 25° C. to induce red blood cell lysis. Following the addition of 500 µL of the lysed sample to 500 µL TCR, no precipitate was observed. Target capture was performed as generally described in U.S. Pat. No. 6,110,678. Babesia 18S rRNA was detected in each sample by transcription-mediated amplification (U.S. Pat. Nos. 5,399,491, 5,554,516, 5,824,518 and 7,833,716). Primers used to amplify Babesia 18S rRNA in the samples were as follows:

TABLE 1

| FUNCTION | Sequence (5'-3') |
|---|---|
| non T7 Primer | ACAGGGAGGTAGTGACAAG (SEQ ID NO: 1) |
| T7 Primer | AATTTAATACGACTCACTATAGGGAGACTGGAATTACC GCGGCTGCTGG (SEQ ID NO: 2) |
| AE Probe | ACCCUUCCCAGAGUAUCAAU (SEQ ID NO: 3) |
| TCO | GGAUUGGGUAAUUUGCGCGCCTTTAAAAAAAAAAAAAA AAAAAAAAAAAAAAA (SEQ ID NO: 4) |

As shown in FIG. 1, Babesia 18S rRNA was detected in the spiked human whole blood samples at a dilution as low as $1\times10^{-8}$. However, a large variability in performance was observed with regard to the age of the blood (3 to 5 days old). These results suggested that a stabilization component should be included if a buffered ACL solution were to be used for whole blood lysis and detection of Babesia.

Figure 2A:
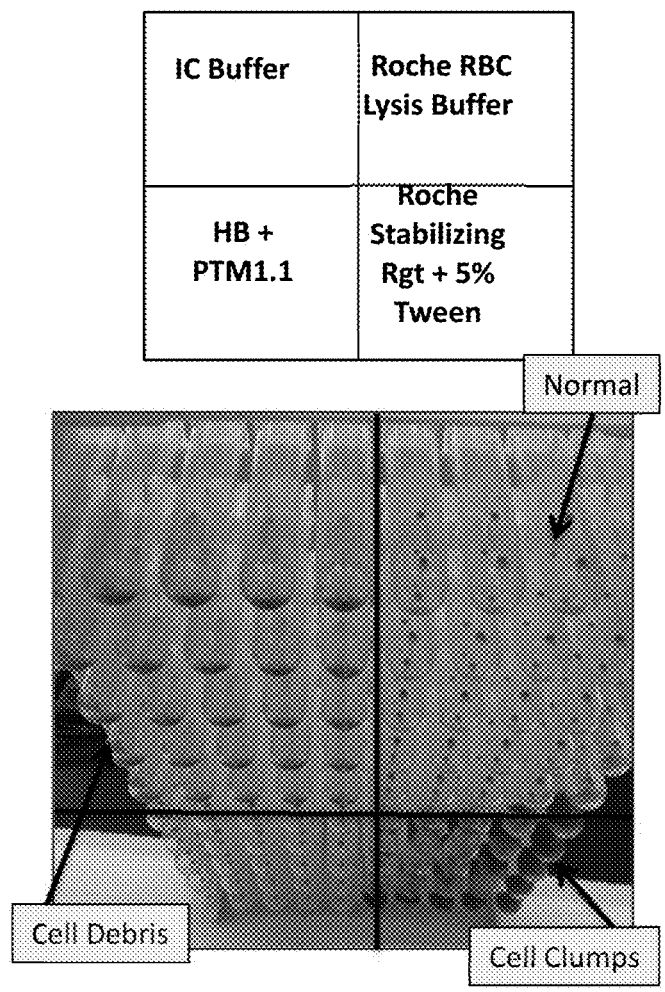
FIGS. 2a, 2b and 2c show analysis of various lysis reagents and their ability to lyse whole blood samples without causing cell precipitation, cell clumping, cell debris, or magnetic bead loss when added to TCR for analysis.
Figure 2B:
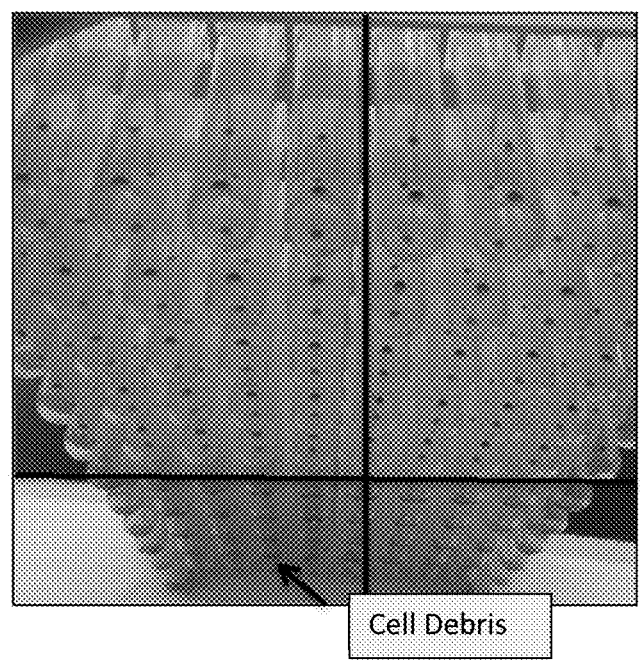
Figure 2C:
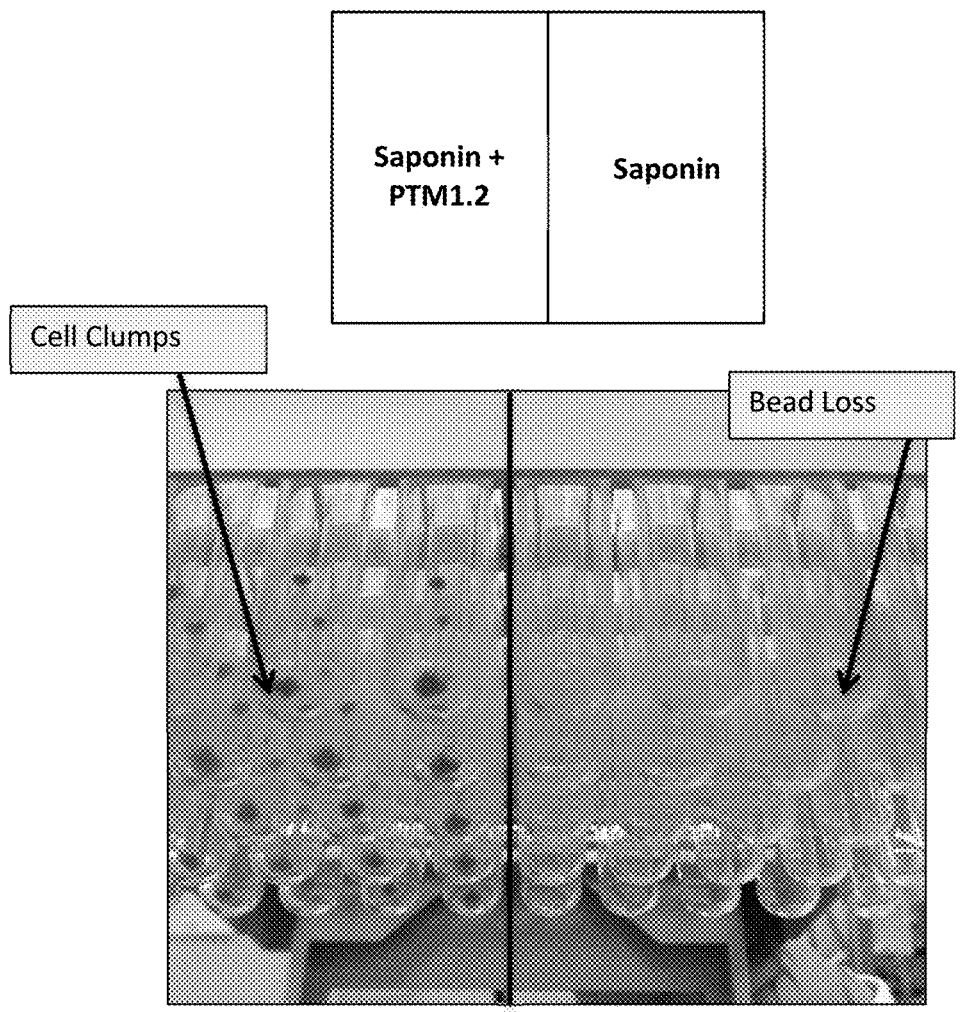

Additional lysis reagents were evaluated for their compatibility with Gen-Probe's Target Capture Technology. Lysis reagents evaluated included: IC Buffer containing 10% lithium lauryl sulfate (LLS); Roche RBC lysis buffer; buffered ACL formulated with 4% tetradecyltrimethylammonium bromide (TDTMAB), 250 mM tartaric acid, and 5% Tween 20 (HB+PTM1.1); Roche Stabilizing Reagent with 5% Tween-20, guanidinium thiocyanate, Triton X-100, and a reducing chemical; 0.2% saponin; 0.2% saponin formulated with 4% TDTMAB, 250 mM tartaric acid, and 10% Tween-20; 4% TDTMAB, 250 mM tartaric acid, and 10% Tween-20; and PAXGENE lysis solution. As shown in FIG. 2, only Roche RBC lysis buffer and IC buffer induced cell lysis in this experiment without the appearance of precipitate or loss of magnetic beads when added to TCR.

Further analysis of different lysis reagents was performed as shown in FIG. 3 for compatibility with Procleix and Aptima TCR solutions (Grifols SA, cat. no. 302573 and Hologic, Inc., cat. no.302178. A number of reagents showed no or diminished activity in one or both TCRs (saponin with and without 5% Tween-20; PAXGENE lysis solution; PTM1.0, 1.1, and 1.2). Some produced precipitate (PPT) when added to a TCR. Others were reasonable candidates in one or both TCRs, while TPM2.4 (250 mM ACL, 14 mM sodium bicarbonate, and 5% LLS) was a good candidate in the Procleix TCR and IC Buffer was a good candidate in both TCRs.

Figure 4:
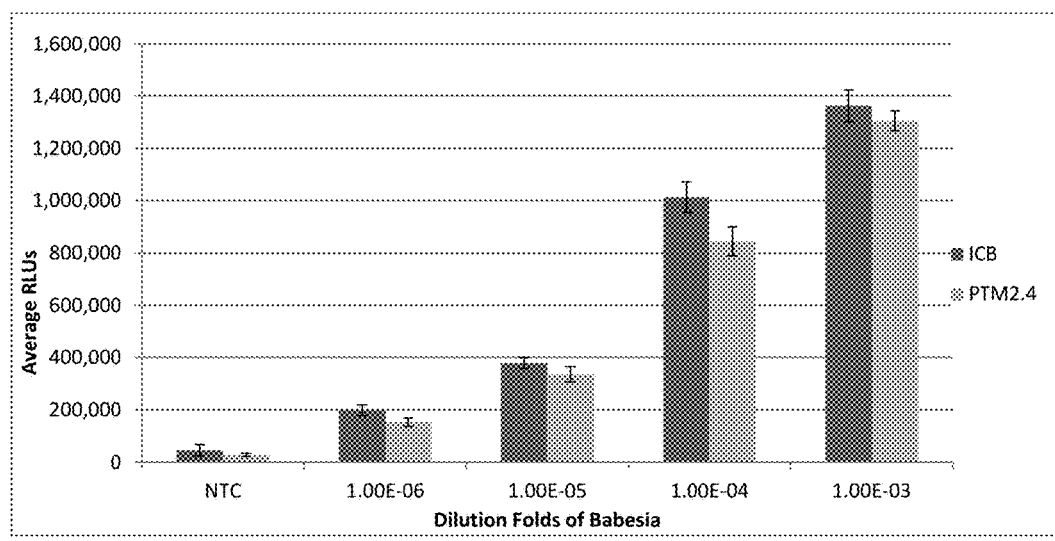
FIG. 4 shows a comparison between PTM2.4 (250 mM ACL, 14 mM sodium bicarbonate, 5% lithium lauryl sulfate (LLS)) and IC buffer (10% LLS) for use in lysing whole blood samples prior to detection of *Babesia* 18S rRNA.

A study using the PTM 2.4 solution and IC buffer (10% LLS) was performed to compare the effectiveness of these lysis reagents for detecting Babesia. Human whole blood was spiked with Babesia-infected hamster blood at dilutions ranging from $1\times10^{-3}$ to $1\times10^6$. Blood samples were lysed with a lysis reagent of buffered ACL and 5% LLS or a lysis reagent of IC buffer at a ratio of 1:3 (blood:reagent). Babesia 18S rRNA was detected in each sample using Procleix TCR and amplification by TMA as described above. As shown in FIG. 4, Babesia 18S rRNA detection is comparable when blood is lysed using PTM2.4 or IC Buffer. However, it was observed in these experiments that, without an initial centrifugation step to pellet red blood cells from whole blood, IC buffer produced cellular debris following the lysis step that could potentially interfere with target capture and magnetic bead wash steps. Therefore, PTM2.4 ("buffered ACL and 5% LLS") was selected for further evaluation.

Example 2

Evaluation of LLS in ACL Lysis Solution

Figure 5:
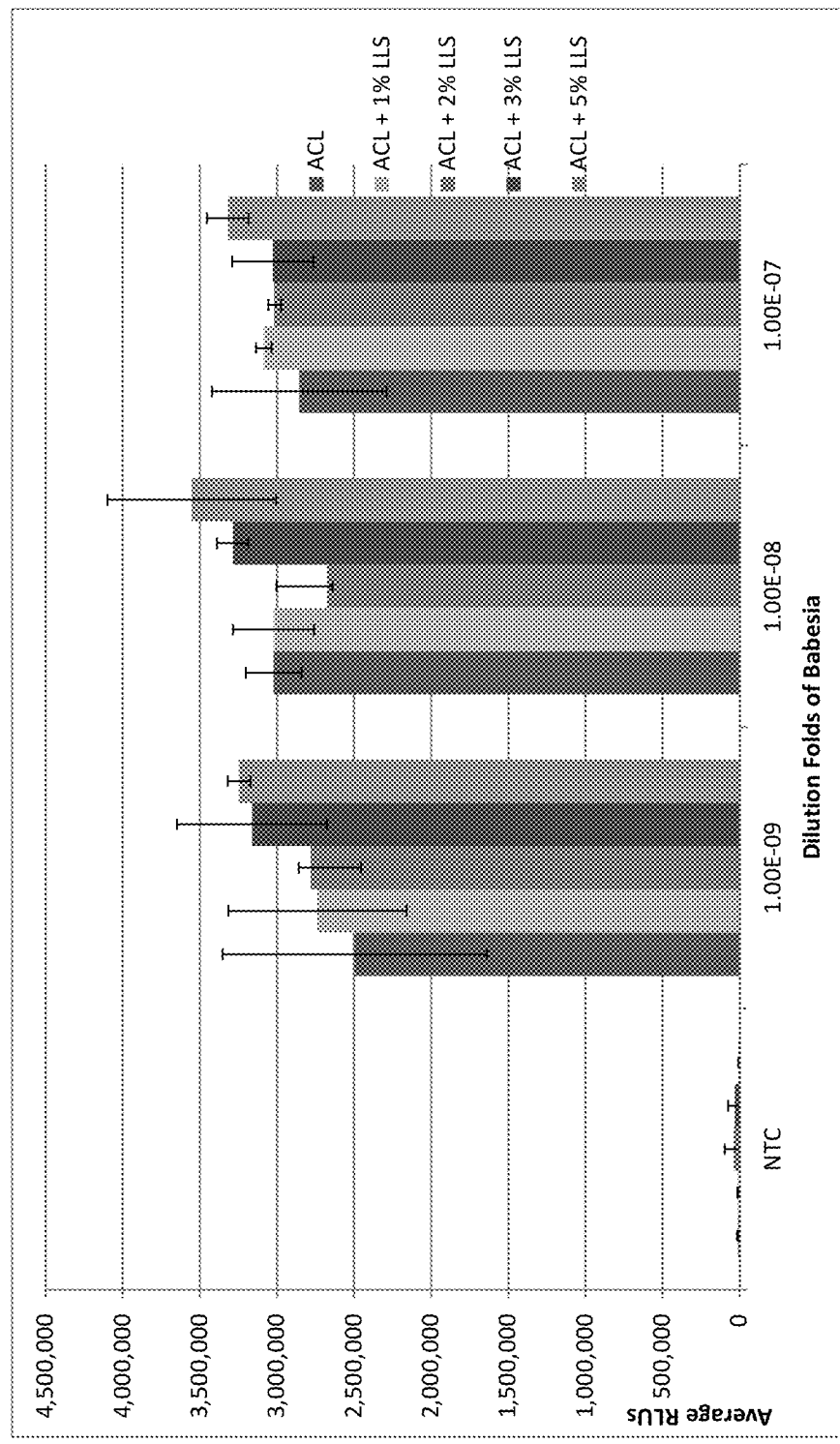
FIG. 5 shows the effect of LLS in the buffered ACL solution for detection of *Babesia* 18S rRNA in whole blood samples.

The necessity of LLS in the buffered ACL solution was examined in this example. LLS was included in the buffered ACL solution at concentrations of 0% (control), 1%, 2%, 3%, and 5%. Human whole blood was spiked with *Babesia*-infected hamster blood at dilutions ranging from $1\times10^{-7}$ to $1\times10^{-9}$. Spiked whole blood samples were lysed with each of the buffered ACL/LLS solutions. *Babesia* 18S rRNA was detected in each sample using Procleix TCR and amplification by TMA as described above. As shown in FIG. 5, a decrease in the concentration of LLS results in greater variability of detection of the *Babesia* 18S rRNA. This is likely due to an insufficient amount of LLS present to stabilize the *Babesia* 18S rRNA target prior to amplification by TMA.

Example 3

Sensitivity of Detection of *Babesia*

Figure 6A:
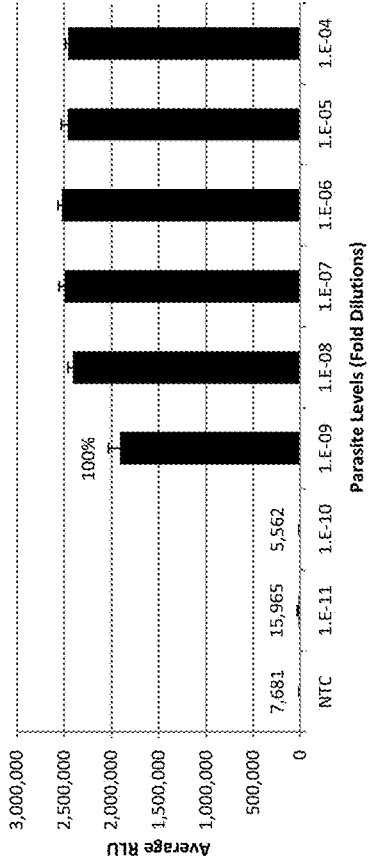
FIG. 6A shows assay sensitivity for detecting *Babesia* 18S rRNA in human whole blood samples spiked with serial dilutions of *Babesia*-infected hamster blood. Samples were lysed with a lysis reagent of buffered ACL and 5% LLS prior to detection). Arbitrary cutoff=50,000 RLU; Any activity >50,000 RLU is considered 100% reactive.

The sensitivity of detecting *Babesia* in human whole blood using buffered ACL and 5% LLS was examined. Human whole blood was spiked with *Babesia*-infected hamster blood at dilutions of $1\times10^{-4}$ to $1\times10^{-11}$. Blood samples were lysed with a lysis reagent of buffered ACL and 5% LLS. *Babesia* 18S rRNA was detected in each sample using Procleix TCR and amplification by TMA as described above. As shown in FIG. 6A, *Babesia* 18S rRNA could be detected in human whole blood at dilutions as low as $1\times10^{-8}$ to $1\times10^{-9}$ when using this lysis reagent and assay protocol.

The number of in vitro transcripts (IVTs) detectable by the method was also determined. The in vitro transcripts used in this experiment had the following sequence:

```
                                        (SEQ ID NO: 5)
GGGCGAAUUGGGUACCGGGCCCCCCUCGAGGUCGACGCUUAGUAUAAGC

UUUUAUACAGCGAAACUGCGAAUGGCUCAUUAAAACAGUUAUAGUUUAUU

UGAUGUUCGUUUUACAUGGAUAACCGUGGUAAUUCUAGGGCUAAUACAUG

CUCGAGGCGCGUUUUCGCGUGGCGUUUAUUAGACUUUAACCAACCCUUCG

GGUAAUCGGUGAUUCAUAAUAAAUUAGCGAAUCGCAUGGCUUUGCCGGCG

AUGUAUCAUUCAAGUUUCUGACCUAUCAGCUUUGGACGGUAGGGUAUUGG

CCACCGGGGCGACGACGGGUGACGGGGAAUUGGGGUUCGAUUCCGGAGAG

GGAGCCUGAGAAACGGCUACCACAUCUAAGGAAGGCAGCAGGCGCGCAAA

UUACCCAAUCCUGACACAGGGAGGUAGUGACAAGAAAUAACAAUACAGGG

CUUAAAGUCUUGUAAUGGAAUGAUGGGAAUCUAAACCCUUCCCAGAGUA

UCAAUUGGAGGGCAAGUCUGGUGCCAGCAGCCGCGGUAAUUCCAGCUCCA

AUAGCGUAUAUUAAAGUUGUUGCAGUUAAGAAGCUCGUAGUUGAAUUUCU

GCCUUGUCAUUAAUCUCGCUUCCGAGCGUUUUUUAUUGACUUGGCAUCU

UCUGGAUUUGGUGCCUUCGGGUACUAUUUUCCAGGAUUUACUUUGAGAAA

ACUAGAGUGUUUCAAACAGGCAUUCGCCUUGAAUACUACAGCAUGGAAUA
```

```
                        -continued
AUGAAGUAGGACUUUGGUUCUAUUUUGUUGGUUAUUGAGCCAGAGUAAUG

GUUAAUAGGAGCAGUUGGGGGCAUUCGUAUUUAACUGUCAGAGGUGAAAU

UCUUAGAUUUGUUAAAGACGAACUACUGCGAAAGCAUUUGCCAAGGAUGU

UUUCAUUAAUCAAGAACGAAAGUUAGGGGAUCGAAGACGAUCAGAUACCG

UCGUAGUCCUAACCAUAAACUAUGCCGACUAGAGAUUGGAGGUCGUCAGU

UUAAACGACUCCUUCAGCACCUUGAGAGAAAUCAAAGUCUUUGGGUUCUG

GGGGGAGUAUGGUCGCAAGUCUGAAACUUAAAGGAAUUGACGGAAGGGCA

CCACCAGGCGUGGAGCCUGCGGCUUAAUUUGACUCAACACGGGAAACCUC

ACCAGGUCCAGACAUAGAGAGGAUUGACAGAUUGAUAGCUCUUUCUUGAU

GAAUU
```

Figure 6B:
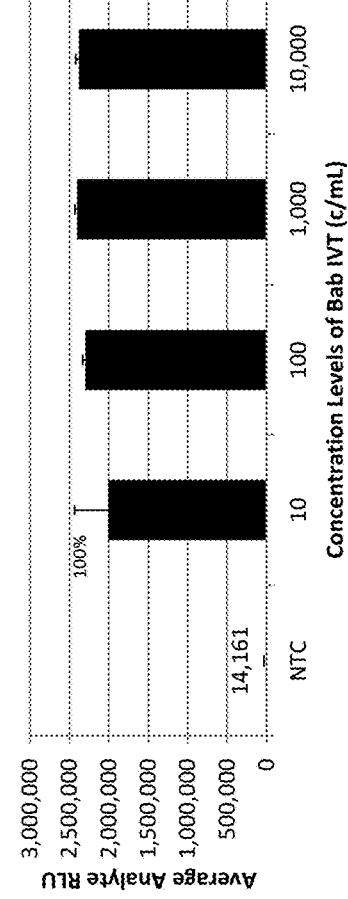
FIG. 6B shows the sensitivity of an assay for detecting *Babesia* 18S rRNA in vitro transcripts spiked into human whole blood. Spiked samples were lysed with a lysis reagent of buffered ACL and 5% LLS prior to detection). Arbitrary cutoff=50,000 RLU; Any activity >50,000 RLU is considered 100% reactive.

The analytical sensitivity of the assay was determined by using in vitro transcripts (IVT) of the *Babesia* 18s rRNA target. 10, 100, 1000, or 10,000 IVT copies of *Babesia* 18S rRNA were spiked into IC buffer. IVT was detected using Procleix TCR and procedure to capture the IVT, followed by TMA amplification of the captured IVT, as described above. As shown in FIG. 6B, as few as 10 IVT copies per mL could be detected.

The number of *Babesia* parasites detectable by the assay was calculated based on these results. As indicated from a parasitemic smear of *Babesia*-infected hamster blood, approximately $5.04\times10^6$ out of $7.20\times10^6$ red blood cells per uL were infected (~70% of RBCs). Thus, at a dilution of $1\times10^{-6}$ to $1\times10^{-7}$, where *Babesia* 18S rRNA is detectable by the assay using buffered ACL and 5% LLS, approximately 1-10 parasites were detectable in a volume of 1 mL of spiked human whole blood sample. As shown in FIG. 6A, the method can detect *Babesia* 18S rRNA at dilutions as low as $1\times10^{-9}$, indicating that the sensitivity of the method can be as low as 1-10 parasites per 100 mL of sample, or lower, correlating to $2\times10^3$ to $2\times10^4$ 18 s rRNA copies per 100 mL of human whole blood.

Example 4

Determining the Optimal Ratio of Blood to Lysis Reagent

Figure 7:
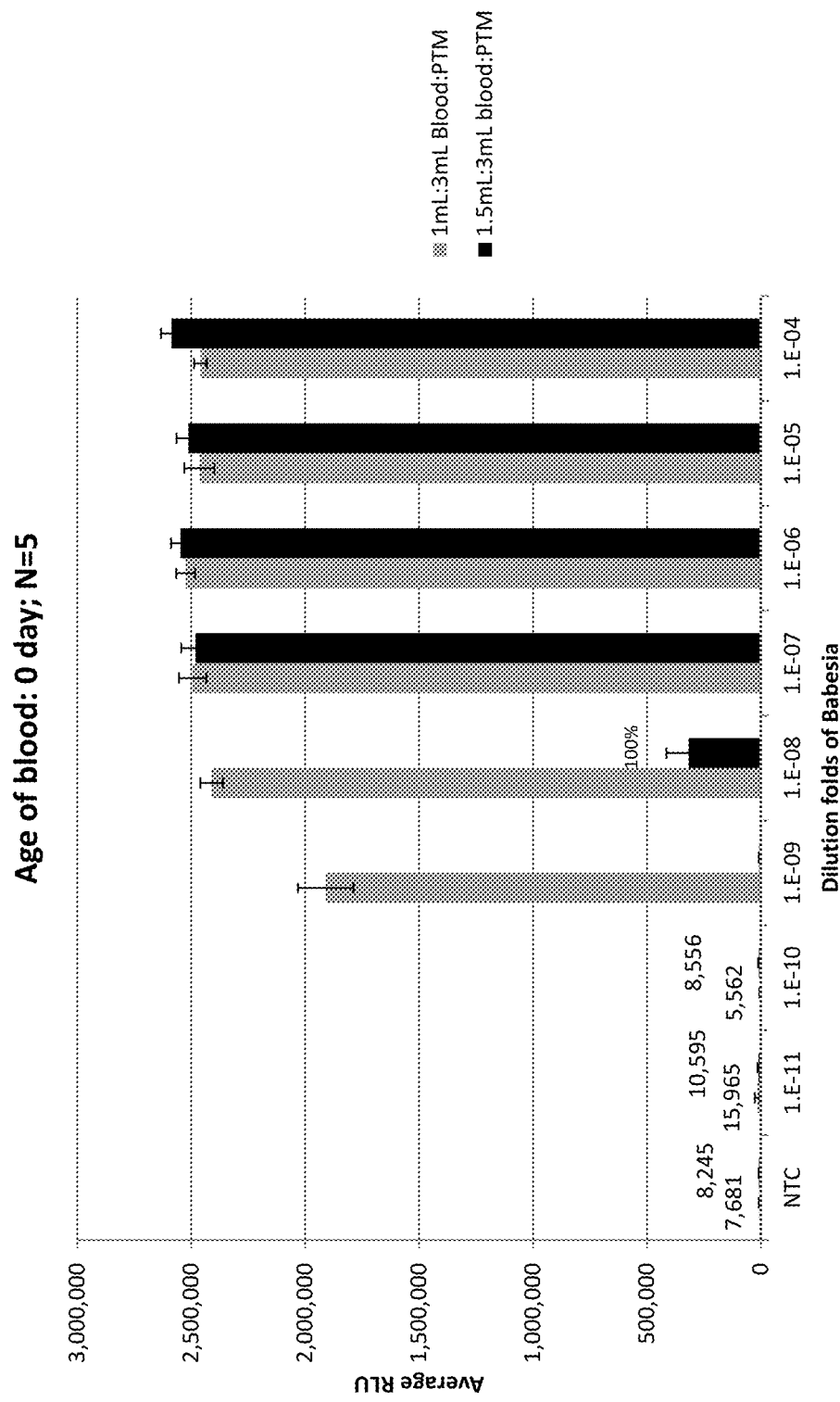
FIG. 7 shows a comparison between two ratios of lysis reagent to human whole blood for the detection of *Babesia* 18S rRNA. A lysis reagent of buffered ACL and 5% LLS was used for cell lysis. The ratios of human whole blood to lysis reagent evaluated in the experiment were 1:2 and 1:3 (blood:reagent). Arbitrary cutoff=50,000 RLU; Any activity >50,000 RLU is considered 100% reactive.

The purpose of this example was to determine the optimal ratio of whole blood to lysis reagent for use in the method. Human whole blood was spiked with *Babesia*-infected hamster blood at a dilution ranging from $1\times10^{-4}$ to $1\times10^{-11}$. The samples were then lysed with a lysis reagent of buffered ACL and 5% LLS at a ratio of 1:2 or 1:3 (blood:reagent). *Babesia* 18S rRNA was detected in each sample using Procleix TCR and amplification by TMA as described above. As shown in FIG. 7, a ratio of 1:3 (blood:reagent) was superior for the detection of low concentrations of *Babesia* in human whole blood, with sensitivity as low as $1\times10^{-9}$. By contrast, the sensitivity of detection was reduced when using a ratio of 1:2 (blood:reagent).

Example 5

Reproducibility of *Babesia* Detection Between Samples

Figure 8:
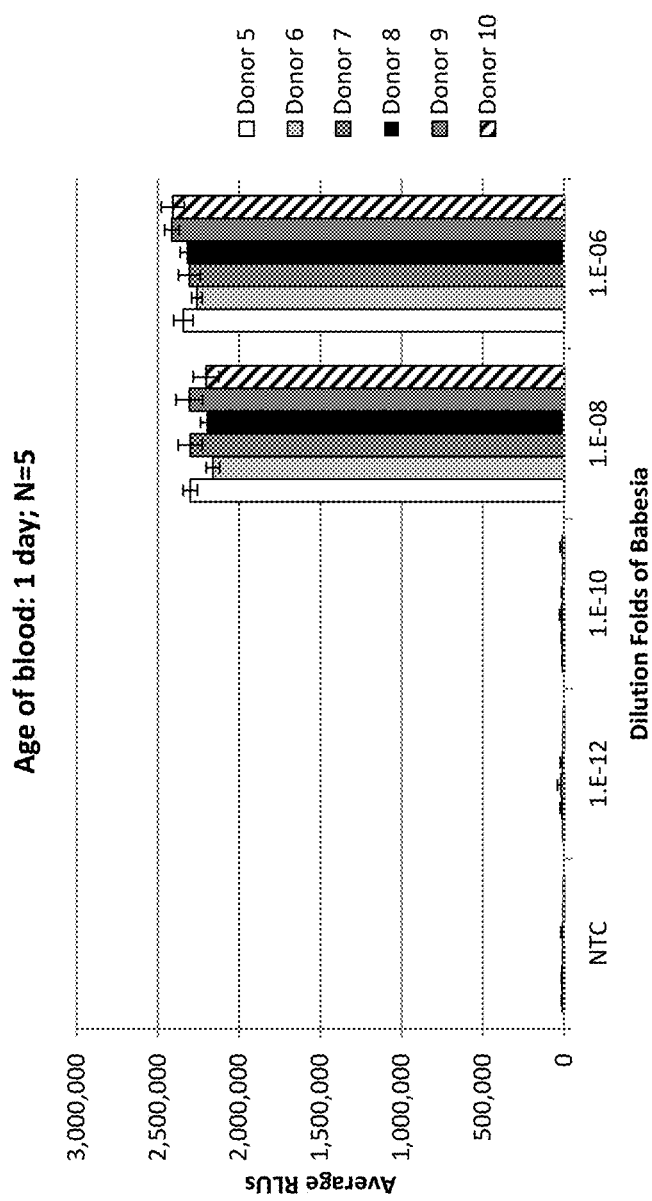
FIG. 8 shows reproducibility of an assay for detecting *Babesia* 18S rRNA in human whole blood samples obtained from 6 different donors. Arbitrary cutoff=50,000 RLU; Any activity >50,000 RLU is considered 100% reactive.

The reproducibility of the *Babesia* detection assay was determined across multiple samples of donor blood. In this experiment, human whole blood was collected from six different donor patients. Each sample was spiked with *Babesia*-infected hamster blood at dilutions between $1\times10^{-6}$ to $1\times10^{-12}$. Samples were then lysed with a lysis reagent of buffered ACL and 5% LLS. *Babesia* 18S rRNA was detected in each sample using Procleix TCR and amplification by TMA as described above. As shown in FIG. 8, use of the lysis reagent with this protocol produced excellent reproducibility between different donor samples for the detection of *Babesia* 18S rRNA at dilutions as low as $1\times10^{-6}$ and $1\times10^{-8}$.

Example 6

Stability of *Babesia* Parasites and Nucleic Acids

Figure 9:
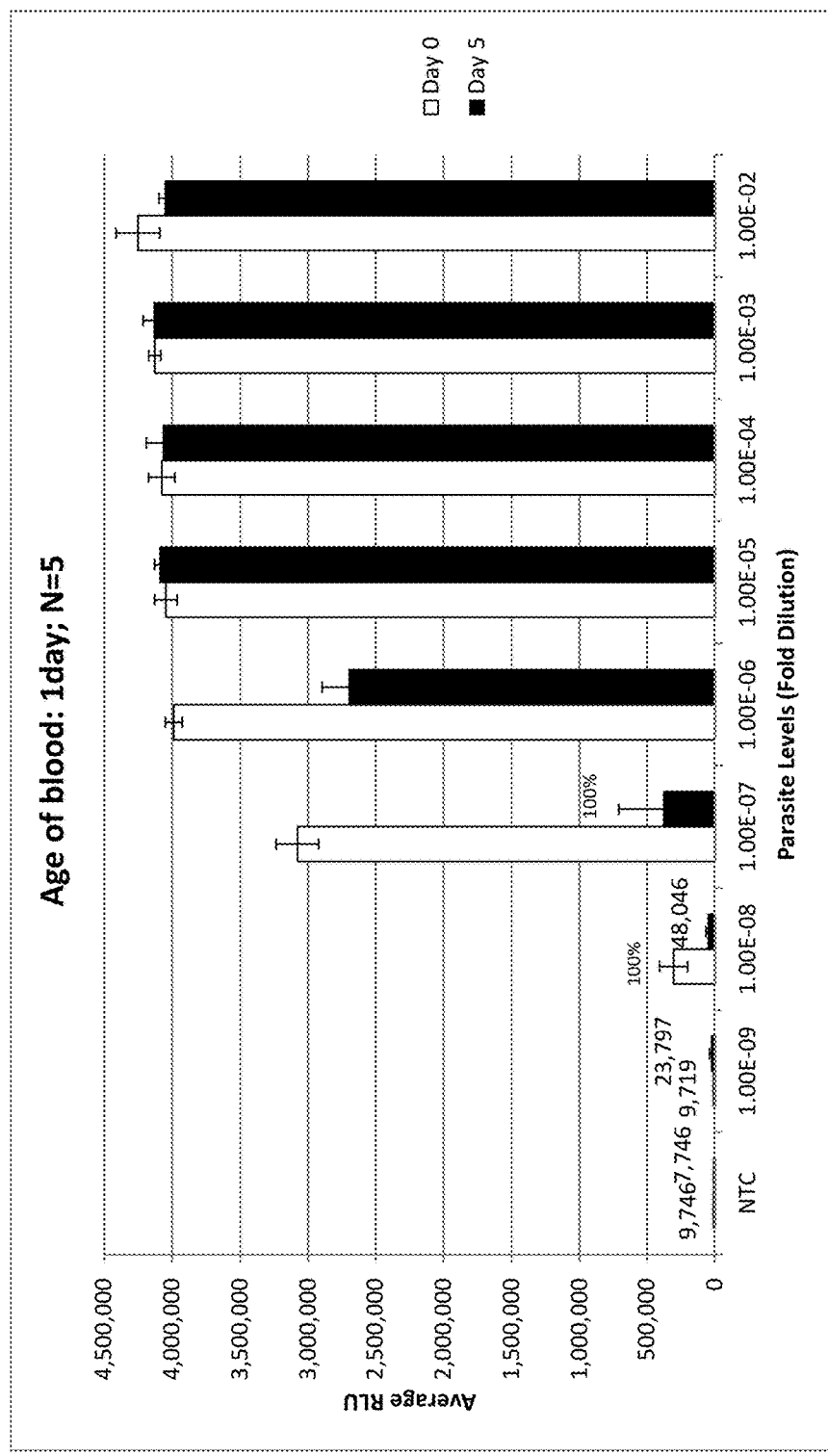
FIG. 9 shows stability of *Babesia* parasites in human whole blood. Serial dilutions of *Babesia*-infected hamster blood were spiked into human whole blood. One group was stored for 5 days at 25° C. prior to analysis. Another group was analyzed immediately after addition of the parasite-infected blood. The infected whole blood samples were lysed with a lysis reagent of buffered ACL and 5% LLS prior to detection of *Babesia* 18S rRNA. Arbitrary cutoff=50,000 RLU; Any activity >50,000 RLU is considered 100% reactive.

Experiments were conducted to determine the stability of *Babesia* parasites in human whole blood over time. To determine parasite stability, human whole blood was spiked with *Babesia*-infected hamster blood at dilutions ranging from $1\times10^{-2}$ to $1\times10^{-9}$. Prior to analysis, one group of samples was stored at 25° C. for five days after spiking Another group was analyzed the same day that the human whole blood was spiked. Spiked whole blood samples were lysed using a lysis reagent of buffered ACL and 5% LLS. *Babesia* 18S rRNA was detected in each sample using Procleix TCR and amplification by TMA as described above. As shown in FIG. 9, a significant loss of sensitivity was observed after five days of storage at 25° C., particularly at dilutions of $1\times10^{-7}$ and $1\times10^{-8}$.

Figure 10:
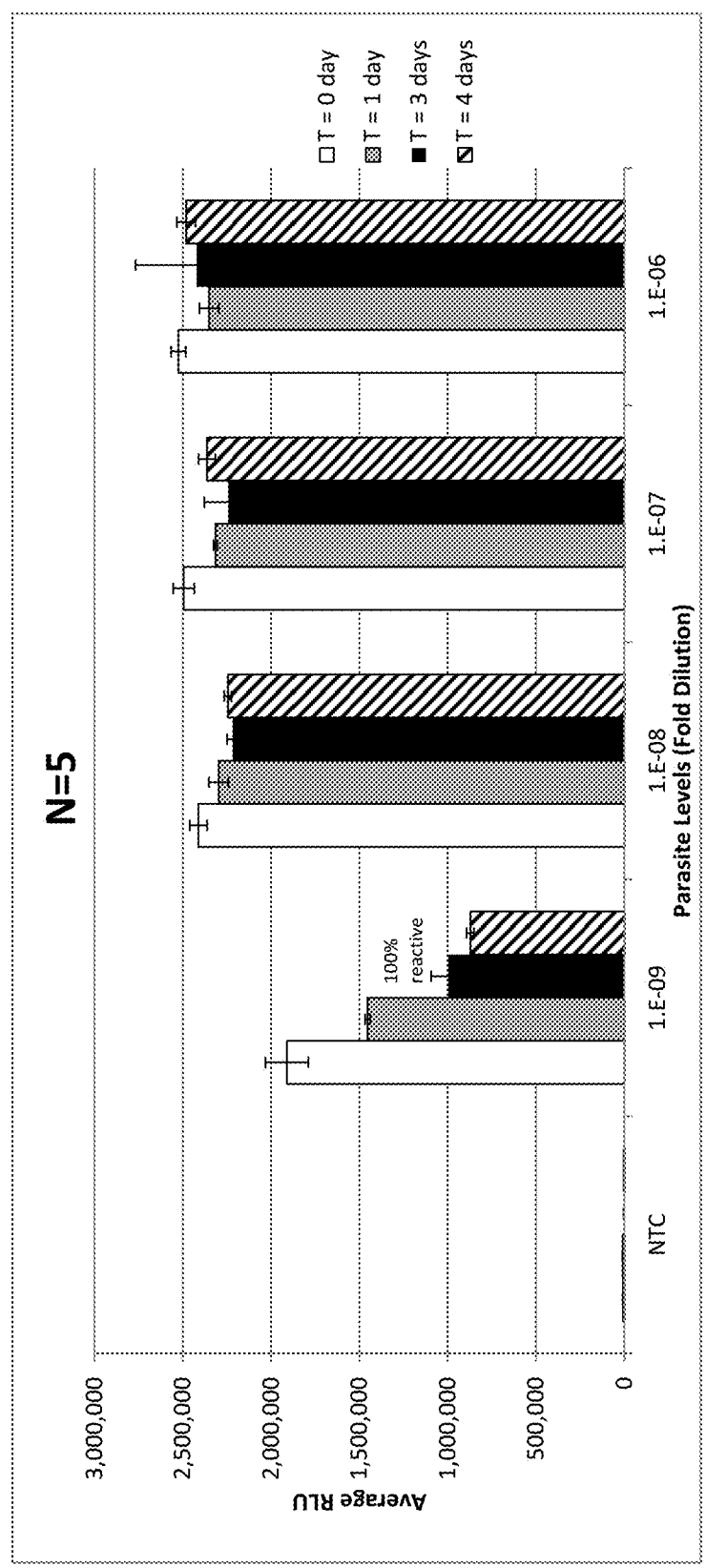
FIG. 10 shows the stability of *Babesia* 18S rRNA released from red blood cells. Serial dilutions of *Babesia*-infected hamster blood were spiked into human whole blood. Samples were lysed with a lysis reagent of buffered ACL and 5% LLS. Following lysis, samples were stored at 4° C. for 0, 1, 3, or 4 days prior to analysis for *Babesia* 18S rRNA. Arbitrary cutoff=50,000 RLU; Any activity >50,000 RLU is considered 100% reactive.

An additional study was performed to determine the stability of *Babesia* 18S rRNA in samples following RBC lysis. Human whole blood was spiked with *Babesia*-infected hamster blood at dilutions ranging between $1\times10^{-6}$ to $1\times10^{-9}$. The samples were lysed using a lysis reagent of buffered ACL and 5% LLS. Lysed samples were stored at 4° C. for 0-4 days prior to analysis. *Babesia* 18S rRNA was detected in each sample using Procleix TCR and amplification by TMA as described above. As shown in FIG. 10, a loss of sensitivity was observed following storage at 4° C., particularly after three and four days. This loss in sensitivity was readily observable in samples having a dilution of $1\times10^{-9}$.

Although the invention has been described in detail for purposes of clarity of understanding, certain modifications may be practiced within the scope of the appended claims. All publications including accession numbers, websites and the like, and patent documents cited in this application are hereby incorporated by reference in their entirety for all purposes to the same extent as if each were so individually denoted. To the extent difference version of a sequence, website or other reference may be present at different times, the version associated with the reference at the effective filing date is meant. The effective filing date means the earliest priority date at which the accession number at issue is disclosed. Unless otherwise apparent from the context any element, embodiment, step, feature or aspect of the invention can be performed in combination with any other.

What is claimed is:

1. A method of analyzing a target RNA from red blood cells comprising:
(a) contacting red blood cells with a reagent comprising ammonium chloride at a concentration of 200-300 mM and lithium lauryl sulfate (LLS) at a concentration of 4% to 15% (w/v), the reagent being effective to lyse the red blood cells and inhibit degradation of target RNA released from the red blood cells; and
(b) analyzing the target RNA released from the red blood cells, wherein said analyzing comprises performing an amplification reaction to amplify the target RNA.

2. The method of claim 1, wherein the target RNA is a pathogen-derived target.

3. The method of claim 1, wherein analyzing the target RNA further comprises contacting the released target RNA with a capture probe and an immobilized probe prior to performing the amplification reaction, the capture probe having a first segment complementary to the target RNA, and a second segment complementary to the immobilized probe, wherein the target RNA binds to the capture probe, and wherein the bound capture probe binds to the immobilized probe.

4. The method of claim 3, wherein the amplification reaction is a transcription mediated amplification reaction and analyzing the target RNA further comprises detecting the resulting amplification product with a detection probe.

5. The method of claim 1, wherein the target RNA is 18S rRNA from a pathogenic organism of the genus *Babesia*.

6. The method of claim 5, wherein the pathogenic organism is of the species *Babesia microti*.

7. The method of claim 6, wherein the limit of detection is at least $2 \times 10^3$ copies of *Babesia microti* 18S rRNA per 1 mL of whole blood.

8. The method of claim 1, wherein the concentration of lithium lauryl sulfate (LLS) is 5% to 8% (w/v).

9. The method of claim 1, wherein the reagent further comprises an anti-coagulant.

10. The method of claim 8, wherein the reagent further comprises sodium bicarbonate buffer.

11. The method of claim 10, wherein the pH of the buffer is 7-8.

12. The method of claim 9, wherein the anti-coagulant is EDTA, heparin, or citrate.

13. The method of claim 8, wherein the concentration of ammonium chloride is 250 mM.

14. The method of claim 9, wherein the concentration of LLS is 5% (w/v).

15. The method of claim 10, wherein the concentration of sodium bicarbonate is 10-20 mM.

16. The method of claim 1, wherein the reagent is admixed with whole blood at step (a) in a ratio of 3:1 (v/v).

17. A method of analyzing a target RNA from red blood cells comprising:
    (a) contacting red blood cells with a reagent comprising ammonium chloride at a concentration of 100-500 mM, lithium lauryl sulfate (LLS) at a concentration of 4% to 15% (w/v), and sodium bicarbonate buffer at a concentration of 10-20 mM and at pH 7-8, the reagent being effective to lyse the red blood cells and inhibit degradation of target RNA released from the red blood cells; and
    (b) analyzing the target RNA released from the red blood cells, wherein said analyzing comprises performing an amplification reaction to amplify the target RNA.

18. The method of claim 17, wherein the reagent further comprises an anti-coagulant.

19. The method of claim 17, wherein analyzing the target RNA further comprises contacting the released target RNA with a capture probe and an immobilized probe prior to performing the amplification reaction, the capture probe having a first segment complementary to the target RNA, and a second segment complementary to the immobilized probe, wherein the target RNA binds to the capture probe, and wherein the bound capture probe binds to the immobilized probe.

20. The method of claim 17, wherein the concentration of lithium lauryl sulfate (LLS) is 5% to 8% (w/v).

* * * * *

SEQUENCE LISTING

```
<160> NUMBER OF SEQ ID NOS: 5

<210> SEQ ID NO 1
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 1
acagggaggt agtgacaag                                                 19

<210> SEQ ID NO 2
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: promoter
<222> LOCATION: (1)..(27)

<400> SEQUENCE: 2
aatttaatac gactcactat agggagactg gaattaccgc ggctgctgg              49

<210> SEQ ID NO 3
<211> LENGTH: 20
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(20)
<223> OTHER INFORMATION: 2' O-Methyl

<400> SEQUENCE: 3
```

-continued

```
acccuuccca gaguaucaau                                                      20

<210> SEQ ID NO 4
<211> LENGTH: 54
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (1)..(21)
<223> OTHER INFORMATION: 2' O-Methyl

<400> SEQUENCE: 4
ggauugggua auuugcgcgc ctttaaaaaa aaaaaaaaaa aaaaaaaaaa aaaa              54

<210> SEQ ID NO 5
<211> LENGTH: 1205
<212> TYPE: RNA
<213> ORGANISM: Artificial Sequence
<220> FEATURE:
<223> OTHER INFORMATION: Synthetic Oligonucleotide

<400> SEQUENCE: 5
gggcgaauug gguaccgggc cccccucga ggucgacgcu aguauaagc uuuuauacag           60 cgaaacugcg aauggcucau uaaaacaguu auaguuuauu ugauguucgu uuuacaugga        120
uaaccguggu aauucuaggg cuaauacaug cucgaggcgc guuucgcgu ggcguuuauu         180 agacuuuaac caacccuucg gguaaucggu gauucauaau aaauuagcga aucgcauggc        240
uuugccggcg auguaucauu caaguuucug accauacagc uuuggacggu agguauugg        300 ccaccggggc gacgacgggu gacggggaau uggggunaga uuccggagag ggagccugag       360
aaacggcuac cacaucuaag gaaggcagca ggcgcgcaaa uuacccaauc cugacacagg       420
gagguaguga caagaaauaa caauacaggg cuuaaagucu uguaauugga augaugggaa       480
ucuaaacccu ucccagagua ucaauuggag ggcaagucug gugccagcag ccgcgguaau      540
uccagcucca auagcguaua uuaaaguugu ugcaguuaag aagcucguag uugaauuucu      600
gccuugucau uaaucucgcu uccgagcguu uuuuauuga cuuggcaucu ucuggauuug      660
gugccuucgg guacuauuuu ccaggauuua cuuugagaaa acuagagugu uucaaacagg      720
cauucgccuu gaauacuaca gcauggaaua augaaguagg acuuugguuuc uauuuuguug      780 guuauugagc cagaguaaug guuaauagga gcaguugggg gcauucguau uuaacuguca      840
gaggugaaau ucuuagauuu guuaaagacg aacuacugcg aaagcauuug ccaaggaugu      900
uuucauuaau caagaacgaa aguuagggga ucgaagacga ucagauaccg ucguaguccu      960
aaccauaaac uaugccgacu agagauugga ggucgucagu uuaaacgacu ccuucagcac     1020
cuugagagaa aucaaagucu uugggucug ggggaguau ggucgcaagu cugaaacuua       1080
aaggaauuga cggaagggca ccaccaggcg uggagccugc ggcuuaauuu gacucaacac     1140
gggaaaccuc accaggucca gacauagaga ggauugacag auugauagcu cuucuugau      1200 gaauu                                                                1205
```